United States Patent [19]

Muto et al.

[11] Patent Number: 5,380,748
[45] Date of Patent: Jan. 10, 1995

[54] TRIALKYLAMINE DERIVATIVE AND AMELIORANT FOR DIGESTIVE TRACT MOVEMENT CONTAINING THE SAME

[75] Inventors: Yoshiaki Muto; Hiromi Ichikawa; Kuniyoshi Ogura; Kyoji Chaki; Masao Seiki; Toshihiko Takemasa, all of Saitama, Japan

[73] Assignee: Zeria Pharmaceutical Co., Ltd., Tokyo, Japan

[21] Appl. No.: 107,825
[22] PCT Filed: Mar. 6, 1992
[86] PCT No.: PCT/JP92/00270
§ 371 Date: Aug. 30, 1993
§ 102(e) Date: Aug. 30, 1993
[87] PCT Pub. No.: WO92/15553
PCT Pub. Date: Sep. 17, 1992

[30] Foreign Application Priority Data

Mar. 7, 1991 [JP] Japan .................. 3-065306

[51] Int. Cl.⁶ .............. A61K 31/38; A61K 31/34; C07D 335/04; C07D 333/50
[52] U.S. Cl. .................. 514/434; 514/443; 514/456; 514/925; 514/926; 514/927; 514/928; 549/23; 549/57; 549/58; 549/396; 549/404; 549/471; 549/50
[58] Field of Search .......... 549/57, 23, 50, 396, 549/404, 471, 58; 514/456, 434, 443, 925, 926, 927, 928

[56] References Cited

U.S. PATENT DOCUMENTS 5,030,736 7/1991 Press et al. .................. 549/50

FOREIGN PATENT DOCUMENTS 2803582 8/1979 Germany .
53-84955 7/1978 Japan .
637363 7/1983 Switzerland .

OTHER PUBLICATIONS

Aboul-Enein et al., *Chemical Abstracts*, vol. 110, No. 15, abstract No. 128064f, 1988.
Sarges et al., *J. Med. Chem.*, vol. 16, No. 9, 1973.

Primary Examiner—Glennon H. Hollrah
Assistant Examiner—Mary C. Cebulak
Attorney, Agent, or Firm—Bacon & Thomas

[57] ABSTRACT

A trialkylamine derivative represented by the formula (1) or a pharmaceutically acceptable salt thereof:

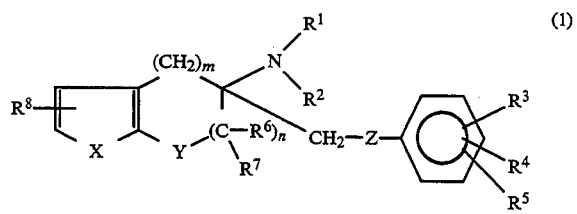

wherein
$R^1$ and $R^2$ may be the same or different from each other and each represents lower alkyl;
$R^3$, $R^4$ and $R^5$ may be the same or different from one another and each represents hydrogen, lower alkyl, lower alkoxy, lower alkoxycarbonyl or halogen;
$R^6$ and $R^7$ may be the same or different from each other and each represents hydrogen or lower alkyl;
$R^8$ represents hydrogen, lower alkyl, lower alkoxy or halogen;
X represents oxygen, sulfur, —CH=N— or —CH=CH—;
Y represents oxygen, sulfur, methylene, N—$R^{11}$ (wherein $R^{11}$ represents lower alkyl), SO or $SO_2$;
Z represents —OCO$(CH_2)_p$~ or —OCH$_2$(CH$_2$)$_p$~ (wherein p represents a number of 0 to 4 and symbol ~ represents the linkage with a benzene ring); and
m and n represent each a number of 0 to 3 and the sum of m and n is 3 or less, provided that the case where m is 0, n is 1 or 2, $R^1$ and $R^2$ represent each methyl, X represents —CH=CH—, Y represents —CH$_2$—, and Z represents —O—CO~ is excluded. These compounds have an excellent activity of ameliorating for gastrointestinal motility and hence are widely utilized in the treatment of gastrointestinal diseases.

5 Claims, No Drawings

TRIALKYLAMINE DERIVATIVE AND AMELIORANT FOR DIGESTIVE TRACT MOVEMENT CONTAINING THE SAME

TECHNICAL FIELD

The present invention relates to trialkylamine derivatives useful in the medical field, and more particularly, to trialkylamine derivatives capable of significantly ameliorating the digestive tract movement (gastrointestinal motility), intermediates for preparing the derivatives, and ameliorants for gastrointestinal motility.

BACKGROUND ART

Hitherto, trimebutine maleate has been primarily used as an ameliorant for gastrointestinal motility.

The trimebutine maleate has wide utility due to its two-face activities of promoting and suppressing the gastric movement. However, it is not necessarily satisfactory in that relatively large amounts, i.e., 300 mg per day of dose are required.

To avoid this disadvantage, studies have been conducted in search for ameliorants for gastrointestinal motility which can replace trimebutine maleate.

For example, (1-dimethylaminoindan-1-yl)methyl ester of substituted benzoic acid and (1-dimethylamino-1,2,3,4-tetrahydronaphthalen-1-yl)methyl ester of substituted benzoic acid are reported to have anticonvulsive activity, antiulcer activity and local anesthetic activity ("Scientia Pharmaceutica" vol. 56, pp. 243-250, 1988).

These, however, do not necessarily provide sufficient ameliorating activity on the gastrointestinal motility.

Accordingly, development of drugs which possess more stronger ameliorating activity on the gastrointestinal motility has still been desired.

The present inventors have carried out earnest studies under the mentioned circumstances, and have found that a specified trialkylamine derivatives exhibit excellent ameliorating activity on the gastrointestinal motility leading to completion of the invention.

DISCLOSURE OF THE INVENTION

According to the present invention, there is provided trialkylamine derivatives represented by the formula (1) or pharmaceutically acceptable salts thereof:

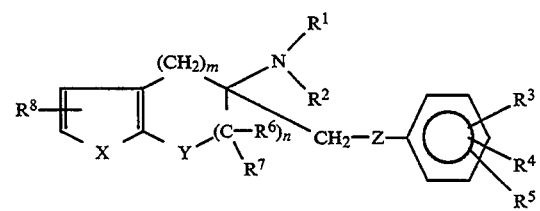
(1)

wherein
$R^1$ and $R^2$ may be the same or different from each other and each represents lower alkyl;
$R^3$, $R^4$ and $R^5$ may be the same or different from one another and each represents hydrogen, lower alkyl, lower alkoxy, lower alkoxycarbonyl or halogen;
$R^6$ and $R^7$ may be the same or different from each halogen;
$R^6$ and $R^7$ may be the same or different from each other and each represents hydrogen or lower alkyl;
$R^8$ represents hydrogen, lower alkyl, lower alkoxy or halogen;
X represents oxygen, sulfur, —CH=N— or —CH=CH—;
Y represents oxygen, sulfur, methylene, >N—$R^{11}$ (wherein $R^{11}$ represents lower alkyl), >SO or >SO$_2$;
Z represents —OCO(CH$_2$)$_p$~ or —OCH$_2$(CH$_2$)$_p$~ (wherein p represents a number of 0 to 4 and symbol ~ represents the linkage with a benzene ring); and
m and n represent each a number of 0 to 3 and the sum of m and n is 3 or less, provided that the case where m is 0, n is 1 or 2, $R^1$ and $R^2$ represent each methyl, X represents —CH=CH—, Y represents —CH$_2$—, and Z represents —O—CO~ is excluded.

The present invention also provides aminoalcohol derivatives represented by the formula (2) or salts thereof:

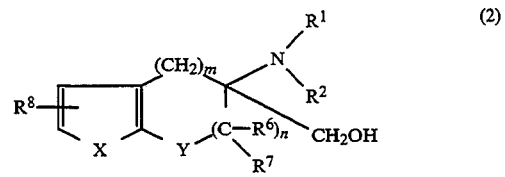
(2)

wherein
$R^1$, $R^2$, $R^6$, $R^7$, $R^8$, X, Y, m and n have the same meaning as defined hereinbefore, provided that the case where X represents —CH=CH—,
Y represents —CH$_2$—,
m is 0 and
n is 1 or 2 is excluded.

The present invention further provides ameliorants for gastrointestinal motility containing, as their active ingredients, trialkylamine derivatives represented by the formula (1):

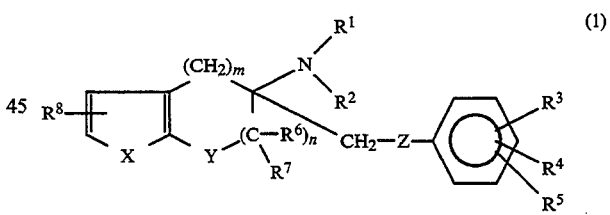
(1)

wherein
$R^1$, $R^2$, $R^3$, $R^4$, $R^5$, $R^6$, $R^7$, $R^8$, X Y, Z, m and n have the same meaning as defined hereinbefore or pharmaceutically acceptable salts thereof.

In the above formulae, the term "lower" means that the number of carbon atoms is 1 to 4, and the term "halogen" means fluorine, chlorine, bromine and iodine.

BEST MODE FOR CARRYING OUT THE INVENTION

The trialkylamine derivatives (1) according to the present invention can be prepared as follows:

First, aminoalcohol derivatives (2), which are the intermediates in the preparation of trialkylamine derivatives (1) of the present invention, are prepared, for example, by the following process. The reaction scheme is shown below:

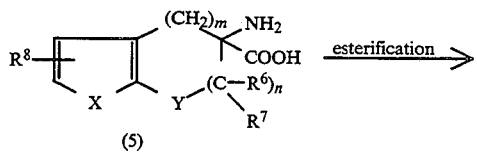

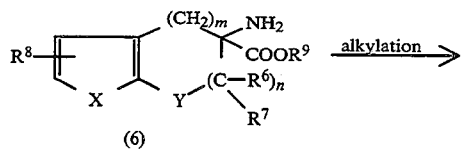

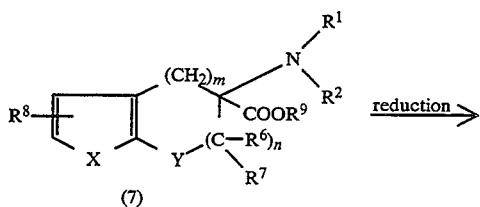

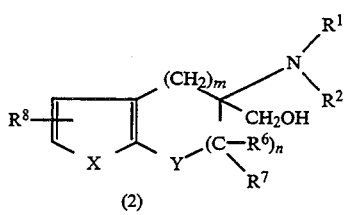

wherein

R⁹ represents lower alkyl, X, Y, R¹, R², R⁶, R⁷, R⁸, m and n have the same meaning as defined hereinbefore.

In detail, the amino acid compound (5) is first esterified to obtain compound (6) by a conventional method, and the amino group of the compound (6) is dialkylated to obtain an ester (7), followed by reducing the ester (7) to produce amino alcohol derivative (2). The reduction is carried out in a solvent and in the presence of a reducing agent at −30° to 80° C. Examples of preferable solvents include ether-series solvents such as diethylether, tetrahydrofuran and dioxane; alcohol-series solvents such as methanol, ethanol, propanol, isopropanol, butanol, isobutanol, sec-butanol and tert-butanol, and mixtures of ether-series solvents and alcohol-series solvents. Examples of preferable reducing agents include suitable selections from hydride-series reducing agents such as lithium aluminum hydride, sodium borohydride, lithium triethylborohydride, aluminum diisobutyl hydride, lithium borohydride and diborane.

Among the aminoalcohol derivatives (2), compounds containing a sulfur atom as Y can be coverted to sulfoxides or sulfones by oxidizing the compounds in accordance with a conventional method.

It is preferred that the oxidizing agents be metachloro perbenzoic acid, hydrogen peroxide, sodium periodate, peroxosulfates and the like.

Among the trialkylamine derivatives (1) of the present invention, those containing a group —O—CO~ (~ has the same meaning as defined above) as Z can be prepared by reacting the aminoalcohol derivatives (2), which are the intermediates of the process, with carboxylic acid compounds represented by the formula (3):

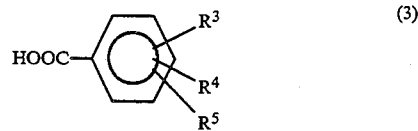

wherein

R³, R⁴, and R⁵ have the same meaning as defined above or their reactive derivatives such as acid halogenides, acid anhydrides, mixed acid anhydrides and active esters.

When the reactive derivatives of carboxylic acids (3) are employed, the reaction is performed in a solvent and in the presence or absence of a basic compound at −30° to 100° C.

No particular limitation is imposed on the solvents as long as they do not adversely affect the reaction. Examples of preferable solvents include ether-series solvents such as diethylether, tetrahydrofuran and dioxane; halogenated hydrocarbon-series solvents such as dichloromethane, dichloroethane, chloroform and carbon tetrachloride; aromatic hydrocarbon-series solvents such as benzene, toluene and xylene; acetonitrile, dimethylformamide, dimethylsulfoxide and water. Examples of preferable basic compounds include trialkylamine, pyridine, alkali metal carbonate, alkali metal hydrogen-carbonate and alkali metal hydroxide.

When the carboxylic acid compounds (3) are used in the form of free caroxylic acids, it is preferred to use a condensing agent. Examples of preferable condensing agents include carbodiimides such as N, N′-dicyclohexylcarbodiimide, N-ethyl-N′-(3-dimethylaminopropyl)-carbodiimide and its hydrochloride and carbonyldiimidazole.

Among the compounds (1) of the present invention, those containing —O—CH₂~ (wherein ~ has the same meaning as defined above) as Z can be prepared by reacting aminoalcohol derivatives (2) with benzyl compounds represented by the formula (4):

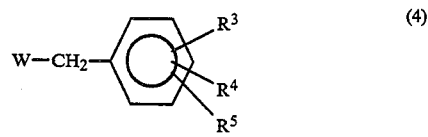

wherein

W represents a reactive residue and R³, R⁴ and R⁵ have the same meaning, respectively.

Examples of the reactive residue represented by W in the benzyl compounds (4) include halogen, methanesulfonyloxy, alkylsulfonyloxy, p-toluenesulfonyloxy and arylsulfonyloxy.

The above reaction is carried out in a solvent and in the presence or absence of a basic compound at 0° to 100° C. No particular limitation is imposed on the solvents useful in the present invention as long as they do not adversely affect the reaction. Examples of preferable solvents include ether-series solvents such as diethylether, tetrahydrofuran and dioxane; aromatic hydrocarbon-series solvents such as benzene, toluene and xylene; dimethylformamide and dimethylsulfoxide. Examples of preferable basic compounds include alkali metal hydride, alkali metal alkoxide and alkali metal hydroxide.

Compounds having a sulfur atom as Y in the compounds (1) of the present invention can be oxidized to sulfoxides or sulfones by conventional methods.

Preferable examples of the oxidizing agents include metachloroperbenzoic acid, hydrogen peroxide, sodium periodate and peroxosulfates.

Examples of the pharmaceutically acceptable salts of the compounds (1) of the present invention include inorganic acid salts such as hydrochlorides, hydrobromides, sulfates and phosphates and organic acid salts such as succinates, maleates, fumarates, tartrates, oxalates, methanesulfonates and paratoluenesulfonates.

Since the compounds (1) according to the present invention possess asymmetric carbon atoms, the compounds may have optical isomers or stereochemical isomers. The present invention encompasses these isomers, too.

The compounds (1) according to the present invention or their pharmaceutically acceptable salts have an action of ameliorating gastrointestinal motility.

In order to formulate ameliorants for gastrointestinal motility from the compounds (1) of the present invention or their pharmaceutically acceptable salts, the compounds are blended with pharmaceutically acceptable adjuvants and prepared to take suitable forms for oral-route administration or non-oral route administration.

In the manufacture of oral-route preparations, the mentioned compounds are blended with suitable additives, for example, vehicles such as lactose, mannitol, corn starch and crystalline cellulose; binders such as cellulose derivatives, gum arabic and gelatin; disintegrators such as carboxymethylcellulose calcium and lubricants such as magnesium stearate, and formed into tablets, powders, granules, capsules and the like. These solid preparations may further be coated with coating bases such as hydroxypropylmethylcellulose phthalate, hydroxypropylmethylcellulose acetate succinate, cellulose acetate phthlate and methacrylate copolymers and formed into enteric preparations.

In the manufacture of non-oral route preparations, the compounds of the invention may be combined, for example, with water, ethanol, glycerol or surfactants which are routinely used in the pharmaceutical field and prepared into injection preparations; or combined with suppository bases to form suppositories.

The amounts of administration of the compounds (1) of the present invention vary depending on the age, body weight, state of the disease, aimed effects of the treatment, manner of administration, period of administration, etc. Generally, the compounds are administered in amounts of 1-2000 mg/day, preferably 10-300 mg/day, which are given as divided in 1 to 3 times a day in the case of oral-route administration.

EXAMPLES

The present invention will hereinafter be described in more detail by way of examples, which however should not be construed as limiting the invention thereto.

EXAMPLES 1-21

Preparation examples of aminoalcohol derivative (2), a preparatory intermediate of the present invention, are shown below.

EXAMPLE 1

Preparation of 4-dimethylamino-4-hydroxymethyl-4,5,6,7-tetrahydro-1-benzothiophene The title compound was obtained via the following Steps 1-3.

Step 1: Preparation of 4-amino-4-methoxycarbonyl-4,5,6,7-tetrahydro-1-benzothiophene 22.62 g of 4,5,6,7-tetrahydro-spiro[1-benzothiophen-4,4'-imidazolidine]-2',5'-dione was added to 300 ml of 20% NaOH solution and refluxed for 20 hours under heat. After cooling, the system was made weakly acidic with HCl, then neutralized with an ammonia solution. After filtration, the filtrate was condensed and dried, and the residue was added with 200 ml of methanol and 15 ml of conc. $H_2SO_4$, followed by reflux under heat for 20 hours. After cooling, the solvent was removed under reduced pressure, and to the residue was added water, and then sodium hydrogencarbonate for making the system basic, followed by extracting with chloroform. After the chloroform phase was dried, the solvent was removed to obtain 15.15 g of the title compound as a pale yellow oily product.

The IR and MS data are shown below.
IR(neat)cm$^{-1}$: 1720
MS(m/z): 211(M+)
The chemical formula is shown below.

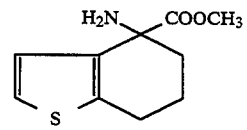

Step 2: Preparation of 4-dimethylamino-4-methoxycarbonyl-4,5,6,7-tetrahydro-1-benzothiophene 25 ml of formic acid containing 9.96 g of 4-amino-4-methoxycarbonyl-4,5,6,7-tetrahydro-1-benzothiophene obtained in Step 1 above was added with 9 ml of 35% formalin solution and heated at 100° C. for 30 minutes. After cooling, the reaction mixture was poured into ice-water, neutralized with sodium hydrogencarbonate and extracted with ether. The ether phase was washed with water and dried. The solvent was removed to obtain 7.80 g of the title compound as pale yellow crystals.

The melting point and MS are shown below.
Melting point: 72°-73° C.
MS(m/z): 239(M+)
The chemical formula is shown below.

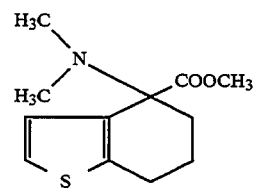

Step 3: Preparation of 4-dimethylamino-4-hydroxymethyl-4,5,6,7-tetrahydro-1-benzothiophene 65 ml of ether solution containing 7.77 g of 4-dimethylamino-4-methoxycarbonyl-4,5,6,7-tetrahydro-1-benzothiophene obtained in Step 2 was added to an ice-cooled suspension of aluminum lithium hydride (1.23 g) in ether, then stirred for 20 minutes at room temperature. The reaction mixture was added with 5% NaOH solution, filtrated to remove the insoluble matters, followed by drying the organic phase.

The solvent was distilled off to obtain 6.58 g of the title compound as colorless crystals.

The melting point, IR, MS and NMR data are shown below.

Melting point: 71°–72° C.
IR(KBr)cm$^{-1}$: 3130
MS(m/z): 211(M+)
NMR(CDCl$_3$)δ: 1.47–1.58(1H,m), 1.71–1.98(3H,m), 2.21(6H,s), 2.74(2H,t), 3.53(1H,d), 3.70(1H,d), 7.04(1H,d), 7.11(1H,d)

The chemical formula is shown below.

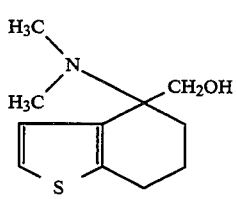

EXAMPLE 2

Preparation of 4-dimethylamino-4-hydroxymethyl-4,5,6,7-tetrahydro-1-benzofuran

The title compound was obtained via the following Steps 1–3.

Step 1: Preparation of 4-amino-4-methoxycarbonyl-4,5,6,7-tetrahydro-1-benzofuran The title compound was obtained by following the procedure of Step 1 in Example 1 except that 4,5,6,7-tetrahydro-spiro[1-benzofuran-4,4'-imidazolidine]-2',5'-dione was used as the starting material.

Step 2: Preparation of 4'-dimethylamino-4-methoxycarbonyl-4,5,6,7-tetrahydro-1-benzofuran 0.9 ml of 35% formalin solution was added to 10 ml of methanol containing 1.00 g of 4-amino-4-methoxycarbonyl-4,5,6,7-tetrahydro-1-benzofuran obtained in Step 1 above. Subsequently, 10% palladium on carbon moistened with water was added to this solution. The reaction was continued for 3 hours in a hydrogen atmosphere, and then the insoluble matters were separated by filtration through celite. The filtrate was dried over anhydrous magnesium sulfate, and the solvent was removed to obtain 1.07 g of the title compound as a pale yellow oily product.

The IR data are shown below.
IR (neat) cm$^{-1}$: 1730
The chemical formula is shown below.

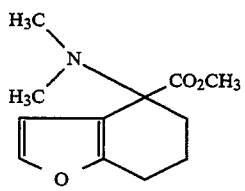

Step 3: Preparation of 4-dimethylamino-4-hydroxymethyl-4,5,6,7-tetrahydro-1-benzofuran The title compound was obtained by following the procedure of Step 3 in Example 1 except that 4-dimethylamino-4-methoxycarbonyl-4,5,6,7-tetrahydro-1-benzofuran obtained in Step 2 was used as the starting material.

The melting point, IR, MS and NMR data are shown below.

Melting point: 91°–92° C.
IR (KBr) cm$^{-1}$: 3200
MS (m/z): (CI) 196 (M+ +1)
NMR (CDCl$_3$) δ: 1.38~1.50 (1H, m), 1.68~2.00 (3H, m), 2.24(6H, s), 2.57 (2H, t), 3.10~3.40 (1H, brs), 3.47 (1H, d), 3.67 (1H, d), 6.43 (1H, d), 7.25 (1H, d)

The chemical formula is shown below.

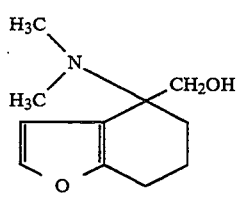

EXAMPLE 3

Preparation of 4-(N-ethyl-N-methyl)amino-4-hydroxymethyl-4,5,6,7-tetrahydro-1-benzothiophene The title compound was obtained by following the Steps 1–3 below.

Step 1: Preparation of 4-N-acetylamino-4-methoxycarbonyl-4,5,6,7-tetrahydro-1-benzothiophene 10.0 g of 4-amino-4-methoxycarbonyl-4,5,6,7-tetrahydro-1-benzothiophene and 5.27 g of triethylamine were dissolved in methylene chloride. 5.32 g of acetic anhydride was added thereto under ice-cooling, then the temperature was returned to room temperature and the mixture was stirred for 30 minutes.

After completion of the reaction, the reaction solution was diluted with ethyl acetate, then washed with 1N HCl and saturated aqueous sodium bicarbonate solution, and dried over anhydrous magnesium sulfate. Subsequently, the solvent was distilled off under reduced pressure to obtain 10.9 g of the title compound as pale brown crystals.

The IR data are shown below.
IR(KBr)cm$^{-1}$: 3265, 1735, 1640
The chemical formula is shown below.

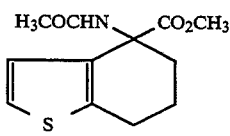

Step 2: Preparation of 4-(N-acetyl-N-methyl)amino-4-methoxycarbonyl-4,5,6,7-tetrahydro-1-benzothiophene To 120 ml of tetrahydrofuran suspended with 4.22 g of 60% sodium hydride was added, under ice-cooling, 120 ml of tetrahydrofuran containing 17.70 g of 4-N-acetylamino-4-methoxycarbonyl-4,5,6,7-tetrahydro-1-benzothiophene as dissolved therein, followed by raising the temperature to room temperature while stirring for 20 minutes. Subsequently, 20 ml of anhydrous tetrahydrofuran containing 8.9 ml of methyl iodide as dissolved was added thereto dropwise, followed by stirring for 3 hours at 50° C.

After completion of the reaction, the reaction solution was condensed under reduced pressure, then poured into ice-water, and extracted with ethyl acetate. The ethyl acetate phase was washed with brine and dried over anhydrous magnesium sulfate, and then distilled off under reduced pressure to obtain 20.98 g of the title compound as a yellow oily product.

The MS data are shown below.
Ms(m/z): 267(M+)
The chemical formula is shown below.

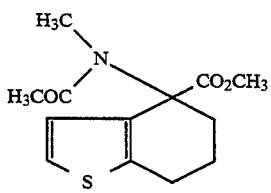

Step 3: Preparation of 4-(N-ethyl-N-methyl)amino-4-hydroxymethyl-4,5,6,7-tetrahydro-1-benzothiophene The title compound (oily product) was obtained by following the procedure of Step 3 in Example 1 except that 4-(N-acetyl-N-methyl)amino-4-methoxycarbonyl-4,5,6,7-tetrahydro-1-benzothiophene obtained in Step 2 was used as the starting material.

The IR, MS and NMR data are shown below.
IR(neat)cm$^{-1}$: 3440, 2935–2800
MS (m/z):(CI)226 (M+ +1)
NMR (CDCl$_3$) δ: 1.03 (3H, t), 1.49~1.59 (1H, m), 1.68~1.96 (3H, m), 2.20 (3H, s), 2.23~2.44 (2H, m), 2.74 (2H, t), 3.49 (1H, brs), 3.49 (1H, d), 3.68 (1H, d), 7.03 (1H, d), 7.10 (1H, d)

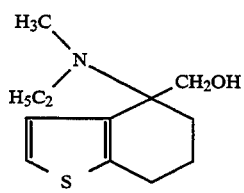

EXAMPLE 4

Preparation of 4-dimethylamino-1-methyl-4-hydroxymethyl-1,2,3,4-tetrahydroquinoline The title compound was obtained via the following Steps 1–3.

Step 1: Preparation of 4-amino-4-methoxycarbonyl-1-methyl-1,2,3,4-tetrahydroquinoline The title compound was obtained by following the procedure of Step 1 in Example 1 except that 1',2',3',4'-tetrahydro-1'-methyl-spiro[imidazolidine-4,4'-quinoline]-2,5-dione was used as the starting material.

Step 2: Preparation of 4-dimethylamino-4-methoxycarbonyl-1-methyl-1,2,3,4-tetrahydroquinoline 1.55 g of 4-amino-4-methoxycarbonyl-1-methyl-1,2,3,4-tetrahydroquinoline obtained in Step 1 was dissolved in 50 ml of dimethylformamide, then added with 2.24 g of methyl iodide and 2.14 g of anhydrous potassium carbonate and the mixture was stirred at room temperature for 15 hours. The reaction mixture was poured into water and extracted with ether. The ether phase was washed with water and dried with anhydrous magnesium sulfate. The solvent was removed to obtain 1.51 g of the title compound as pale yellow crystals.

The melting point, IR and MS data are shown below.
Melting point: 45°–46° C.
IR (KBr)cm$^{-1}$: 1720, 1240, 755
MS (m/z): 248 (M+)
The chemical formula is shown below.

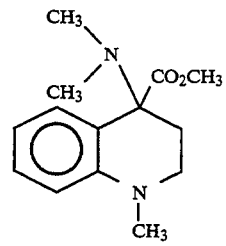

Step 3: Preparation of 4-dimethylamino-4-hydroxymethyl-1,2,3,4-tetrahydroquinoline The title compound was obtained by following the procedure of Step 3 in Example 1 except that 4-dimethylamino-4-methoxycarbonyl-1-methyl-1,2,3,4-tetrahydroquinoline obtained in Step 2 was used as the starting material.

The melting point, IR, MS and NMR data are shown below.
Melting point: 104°–105° C.
IR(KBr)cm$^{-1}$: 1500, 1105, 760
MS (m/z):(FAB)221 (M+ +1)
NMR (CDCl$_3$) δ: 1.71~1.79(1H, m), 2.11~2.22(1H, m), 2.25(3H, s), 2.27(3H, s), 2.55 (1H, bs), 2.88 (3H, s), 3.12~3.28 (2H, m), 3.64(1H, d), 3.74(1H, d), 6.59~6.70(2H, m), 7.12~7.18 (1H, m), 7.57 (1H, dd)

The chemical formula is shown below.

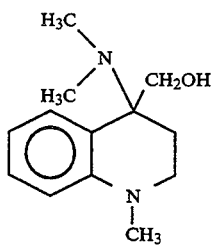

EXAMPLE 5

Preparation of 4-dimethylamino-4-hydroxymethyl-2,3-dihydro-4H-1-benzopyran.HCl

The title compound was obtained by following the procedures of Steps 1-3 in Example 1 except that 2,3-dihydro-spiro[4H-1-benzopyran-4,4'-imidazolidine]-2',5'-dione was used as the starting material, and then converted to a hydrochloride.

The melting point, IR, MS and NMR data are shown below.

Melting point: 216°–217° C.
IR(KBr)cm$^{-1}$: 1060
MS (m/z): 207 (M+)
NMR (CDCl$_3$) δ: 2.05~2.30 (1H, m), 2.40~2.60 (4H, m), 3.08 (3H, d), 4.08~4.17 (2H, m), 4.30~4.40 (1H, m), 4.55~4.70 (1H, m), 6.85~6.94 (1H, m), 7.03~7.15 (1H, m), 7.23~7.35 (1H, m), 7.95~8.05 (1H, m)

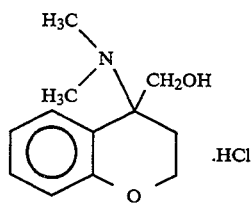

EXAMPLE 6

Preparation of 4-dimethylamino-4-hydroxymethyl-2,3-dihydro-4H-1-benzothiopyran

The title compound was obtained by following the procedures of Steps 1-3 in Example 1 except that 2,3-dihydro-spiro[4H-1-benzothiopyran-4,4'-imidazolidine]-2',5'-dione was used as the starting material.

The melting point, IR, MS and NMR data are shown below.

The melting point: 94°–95° C.
IR (KBr)cm$^{-1}$: 2700~3050
MS (m/z): 223 (M+)
NMR (CDCl$_3$) δ: 2.06~2.23(3H, m),2.28(6H, s),2.87~2.96(1H, m), 3.07~3.17 (1H, m), 3.71 (2H, dd), 7.03~7.15 (3H, m), 7.71~7.74(1H, m)

The chemical formula is shown below.

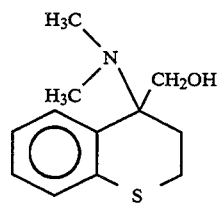

EXAMPLE 7

Preparation of 5-dimethylamino-5-hydroxymethylcyclopenta[b]thiophene

The title compound was obtained by following the procedures of Steps 1-3 in Example 1 except that spiro[cyclopenta[b]thiophene-5,4'-imidazolidine]-2',5'-dione was used as the starting material.

The IR, MS and NMR data are shown below.
IR(neat)cm$^{-1}$: 2780–3070
MS (m/z): 196 (M+)
NMR (CDCl$_3$) δ: 2.27 (6H, s), 2.55~2.74 (2H, m), 2.95(1H, d), 3.09(1H, d), 3.65 (2H, s), 6.76 (1H, d), 7.14~7.15 (1H, m), The chemical formula is shown below.

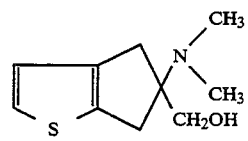

EXAMPLES 8-19

Compounds of the following nomenclature, chemical formulae, melting points, IR, MS and NMR data were obtained by following the procedure of Example 1.

EXAMPLE 8

4-Dimethylamino-4-hydroxymethyl-cyclopenta[b]thiophene

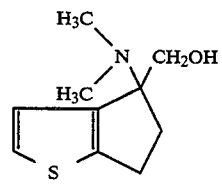

Melting point: 48°–49° C.
IR (KBr) cm$^{-1}$: 3175, 1465, 1040
MS (m/z):(FAB) 198(M+ +1)
NMR (CDCl$_3$) δ: 2.01~2.11(1H, m), 2.18(6H, s), 2.57~2.67(1H, m), 2.87~2.92 (2H, m), 3.00 (1H, brs), 3.57 (1H, d), 3.74(1H, d)

EXAMPLE 9

4-Dimethylamino-4-hydroxymethyl-cyclohepta[b]thiophene.HCl

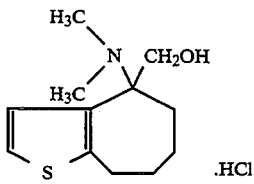

Melting point: 165° C.
IR(KBr) cm⁻¹: 3200
MS (m/z):(CI)226(M++1)
NMR (CDCl₃) δ: 1.42~1.96(4H, m),2.14~2.25(2H, m), 2.56(3H, d), 2.77~2.89 (1H, m), 3.10~3.22 (1H, m), 3.74(1H, dd), 4.10 (1H, dd), 5.95~6.05 (1H, m), 7.33 (1H, d), 7.44 (1H, d) 9.76~9.86 (1H, brs)

EXAMPLE 10

5-Dimethylamino-5-hydroxymethyl-5,6,7,8-tetrahydroquinoline

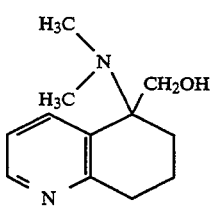

Melting point: 125°-126° C.
IR(KBr) cm⁻¹: 3130
MS (m/z): (CI) 207 (M++1)
NMR (CDCl₃) δ: 1.61~2.03(4H, m), 2.22(6H, s), 2.75~2.79(3H, m), 3.54 (1H, d), 3.76 (1H, d), 7.12 (1H, dd), 7.96 (1H, dd), 8.40 (1H, dd)

EXAMPLE 11

1-Dimethylamino-1-hydroxymethyl-cycloheptabenzene

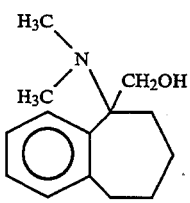

Oily product
IR(neat)cm⁻¹: 3450, 2935-2785
MS (m/z):(CI)220(M++1)
NMR (CDCl₃) δ: 1.34~1.45(1H, m), 1.52~1.80(4H, m), 1.85~2.04 (2H, m), 2.25 (6H, s), 2.82~2.86 (2H, m), 3.74(1H, d), 3.81 (1H, d), 7.08(1H, d), 7.15(1H, dt), 7.21 (1H, dt), 7.76 (1H, d)

EXAMPLE 12

6-Chloro-4-dimethylamino-4-hydroxymethyl-2,3-dihydro-4H-1-benzopyran

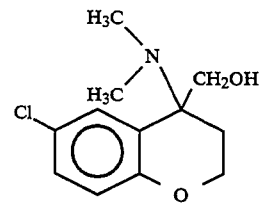

Melting point: 107°-108° C.
IR (KBr)cm⁻¹: 3400, 1485, 1070
MS (m/z):(FAB)242 (M+30 1)
NMR (CDCl₃) δ: 1.71 (1H, m), 2.21 (1H, m), 2.23 (6H, s), 2.81 (1H, brs), 3.67 (1H, d), 3.78 (1H, d), 4.17 (2H, m), 6.76 (1H, d), 7.09 (1H, dd), 7.54 (1H, d)

EXAMPLE 13

4-Dimethylamino-6-fluoro-4-hydroxymethyl-2,3-dihydro-4H-1-benzopyran

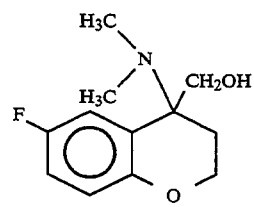

Melting point: 100°-103° C.
IR (KBr) cm⁻¹: 3050~2800, 1490, 1460
MS (m/z):(CI)226(M++1)
NMR (CDCl₃) δ: 1.69 (1H, ddd), 2.16~2.28 (1H, m), 2.23 (6H, s), 2.60 (1H, brs), 3.68 (1H, d), 3.78 (1H, d), 4.06~4.23 (2H, m), 6.77 (1H, dd), 6.86 (1H, ddd), 7.29 (1H, dd)

EXAMPLE 14

4-Dimethylamino-4-hydroxymethyl-6-methoxy-2,3-dihydro-4H-1-benzopyran

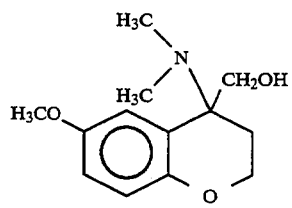

Melting point: 90°-91° C.
IR(KBr)cm⁻¹: 3075~2775, 1580, 1500
MS (m/z): (CI) 238 (M++1),
NMR (CDCl₃) δ: 1.70(1H, ddd), 2.17~2.28 (1H, m), 2.24(6H, s), 2.55 (1H, brs), 3.64~3.81 (2H, m), 3.76 (3H, s), 4.06~4.20 (2H, m), 6.71~6.79 (2H, m), 7.12 (1H, dd)

EXAMPLE 15

4-Dimethylamino-4-hydroxymethyl-6-methyl-2,3-dihydro-4H-1-benzopyran.HCl

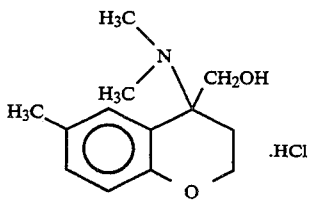

Melting point: 110°–111° C.
IR(KBr) cm$^{-1}$: 3300, 1500, 1230
MS (m/z): (FAB) 222 (M$^+$+1)
NMR (CDCl$_3$) δ: 1.71(1H, m), 2.22(1H, m), 2.23(6H, s), 2.27(3H, s) 2.59 (1H, brs), 3.70 (1H, d), 3.79 (1H, d), 4.14 (2H, m), 6.72 (1H, d), 6.95 (1H, dd), 7.34 (1H, d)

EXAMPLE 16

4-Dimethylamino-4-hydroxymethyl-2,2-dimethyl-2,3-dihydro-4H-1-benzopyran

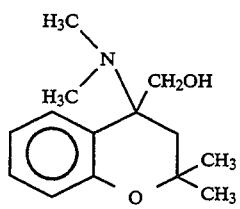

Melting point: 84°–85° C.
IR(KBr)cm$^{-1}$: 3120
MS (m/z) : (CI) 236 (M$^+$+1)
NMR (CDCl$_3$) δ: 1.27(3H, s), 1.39 (3H, s), 1.58(1H, d), 2.10(1H, d), 2.15(6H, s), 3.26~3.46 (1H, brs), 3.76 (2H, s), 6.81 (1H, dd), 6.92 (1H, ddd), 7.15 (1H, ddd), 7.59 (1H, dd)

EXAMPLE 17

6-Chloro-4-dimethylamino-4-hydroxymethyl-2,3-dihydro-4H- 1-benzothiopyran

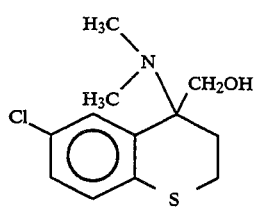

Melting point: 88°–89° C.
IR (KBr)cm$^{-1}$: 3200, 1470, 1080
MS (m/z): (FAB) 258 (M$^+$+1)
NMR (CDCl$_3$) δ:2.12(2H, m), 2.26(6H, s), 2.29(1H, brs),2.89(1H, m), 3.10(1H, m), 3.63 (1H, d), 3.71 (1H, d), 7.05 (2H, m), 7.74 (1H, m)

EXAMPLE 18

4-Dimethylamino-4-hydroxymethyl-6-methoxy-2,3-dihydro-4H-1-benzothiopyran

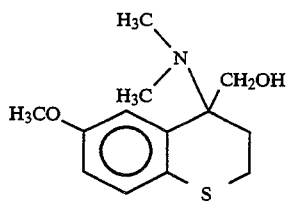

Melting point: 116°–117° C.
IR (KBr)cm$^{-1}$: 3450, 1470, 1290
MS (m/z): (FAB) 254 (M$^+$+1)
NMR (CDCl$_3$) δ: 2.06 (1H, m), 2.19 (1H, m), 2.26 (6H, s), 2.36 (1H, brs), 2.85 (1H, m), 3.08 (1H, m), 3.64 (1H, d), 3.70 (1H, d), 3.76 (3H, s), 6.71 (1H, dd), 7.03 (1H, d), 7.36 (1H, d)

EXAMPLE 19

4-Dimethylamino-4-hydroxymethyl-6-methyl-2,3-dihydro-4H-1-benzothiopyran

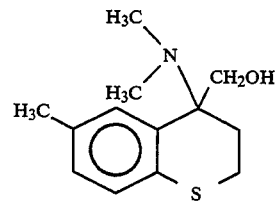

Melting point: 84°–85° C.
IR (KBr)cm$^{-1}$: 3200, 1480, 1080
MS (m/z): (FAB) 238 (M$^+$+1)
NMR (CDCl$_3$) δ: 2.08 (1H, m), 2.20 (1H, m), 2.27 (6H, s), 2.29 (3H, s), 2.88 (1H, m), 3.10 (1H, m), 3.66 (1H, d), 3.73 (1H, d), 6.92 (1H, dd), 7.02 (1H, dd), 7.55 (1H, d)

EXAMPLE 20

Preparation of 4-dimethylamino-4-hydroxymethyl-2,3-dihydro-4H-1-benzothiopyran-1-oxide The title compound was obtained via the following procedure.

248 mg of 70% m-chloroperbenzoic acid was added to a 20 ml of methylene chloride solution containing 222 mg of 4-dimethylamino-4-hydroxymethyl-2,3-dihydro-4H-1-benzothiopyran dissolved therein, and stirred at room temperature for 30 minutes. The reaction solution was washed with 5% aqueous sodium thiosulfate solution, saturated sodium bicarbonate solution and brine in this order, then dried over anhydrous magnesium sulfate. The solvent was removed under reduced pressure, and the crystals were recrystallized from a solvent mixture of ethyl acetate and isopropyl ether. 53 mg of the title compound was obtained as colorless crystals.

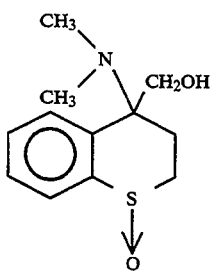

Melting point: 132°–133° C.
IR(KBr)cm⁻¹: 3245, 1070, 1000
MS (m/z): (CI) 240 (M++1)
NMR (CDCl₃) δ: 1.88(1H, m), 2.26(6H, s), 2.40(1H, dd), 2.85(1H, m), 3.01 (1H, m), 3.24 (1H, m), 3.59 (1H, d), 3.73 (1H, d), 7.43 (1H, dt), 7.53 (1H, dt), 7.75 (1H, dd), 7.90 (1H, dd)

EXAMPLE 21

Preparation of 4-dimethylamino-4-hydroxymethyl-2,3-dihydro-4H-1-benzothiopyran-1,1-dioxide The title compound was obtained via the following procedure.

10 g of 4-dimethylamino-4-hydroxymethyl-2,3-dihydro-4H-1-benzothiopyran obtained in Example 6 were suspended in 100 ml of water, to which 50 ml of an aqueous solution of 20 g of potassium peroxomonosulfate was added while stirring under ice cooling. After allowing to react for 1 hour, 3N NaOH solution was added thereto for neutralizing the mixture, followed by extraction with ether. After the ether phase was dried with anhydrous magnesium sulfate, the solvent was condensed to obtain 5.73 g of the title compound as colorless crystals.

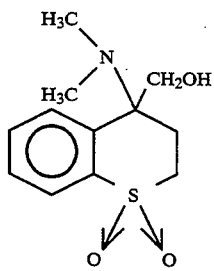

Melting point: 137°–138° C.
IR(KBr) cm⁻¹: 1290, 1130, 760
MS (m/z): 255 (M+)

NMR (CDCl₃) δ: 2.00(1H, brs), 2.25(6H, s), 2.38(1H, ddd), 2.80 (1H, ddd), 3.33 (1H, ddd), 3.62 (1H, ddd), 3.82 (2H, s), 7.40~7.65 (2H, m), 7.85 (1H, dd), 7.96 (1H, dd)

EXAMPLES 22–86

Preparation examples of trialkylamine derivative (1) of the present invention are shown below.

EXAMPLE 22

Preparation of 4-dimethylamino-4-[(3,4,5-trimethoxybenzoyloxy)methyl]-4,5,6,7-tetrahydro-1-benzothiophene 15 ml of pyridine Containing 1.52 g of 4-dimethylamino-4-hydroxymethyl-4,5,6,7-tetrahydro-1-benzothiophene obtained in Example 1 was cooled with ice, and added with 1.82 g of 3,4,5-trimethoxybenzoylchloride. The reaction mixture was then stirred at room temperature for 14 hours. The solvent was removed under reduced pressure, and the residue was poured into water, followed by extracting with chloroform. The chloroform phase was washed with water and dried. The solvent was removed under reduced pressure, and the residue was crystallized from isopropyl ether to obtain 1.87 g of the title compound as colorless crystals.

The melting point, IR, MS and NMR data are shown below.

Melting point: 82°–83° C.
IR(KBr)cm⁻¹: 1710
MS(m/z): 405(M+)
NMR (CDCl₃) δ: 1.68~1.80(1H, m), 1.90~2.10 (3H, m), 2.27(6H, s), 2.77 (2H, t), 3.87 (6H, s), 3.89 (3H, s), 4.41 (1H, d), 4.59 (1H, d), 7.04 (1H, d), 7.14 (1H, d), 7.18 (2H, s)

Hydrochloride of the present product: colorless crystals

Melting point: 201°–202° C. (solvent for recrystalization: chloroform - isopropyl ether )

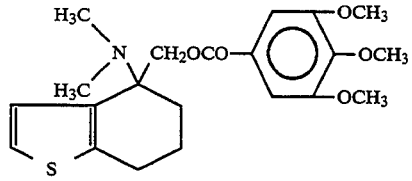

EXAMPLES 23–28

Six kinds of compounds were obtained by following the procedure of Example 22. The chemical formulae, melting points, IR, MS and NMR data of these compounds are shown in Table 1.

TABLE 1-1

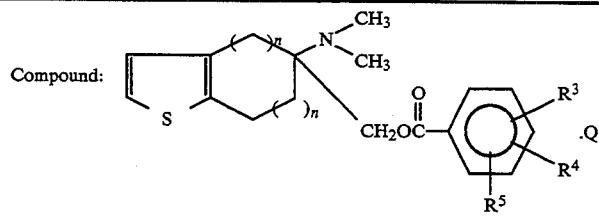

Compound:

| Ex. No. | Q | m | n | R³ | R⁴ | R⁵ | Melting point °C. | MS (m/z) | IR (cm⁻¹) | NMR |
|---|---|---|---|---|---|---|---|---|---|---|
| 23 | — | 1 | 0 | 3-OCH₃ | 4-OCH₃ | 5-OCH₃ | 138~140 | (CI) | (KBr) | (CDCl₃) δ: 2.43(6H, s), 2.84~2.89(1H, m), |

TABLE 1-1-continued

Compound: 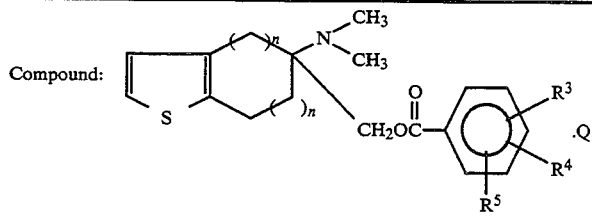

| Ex. No. | Q | m | n | R³ | R⁴ | R⁵ | Melting point °C. | MS (m/z) | IR (cm⁻¹) | NMR |
|---|---|---|---|---|---|---|---|---|---|---|
| | | | | | | | | 392 (M⁺ + 1) | 2750~3100 1695 | 3.02(2H, d), 3.17(1H, d), 3.82(6H, s), 3.88(3H, s), 4.47(2H, s), 6.78(1H, d) 7.13~7.15(3H, m) |
| 24 | HCl | 0 | 2 | 4-OCH₃ | H | H | 194~195 | (CI) 346 (M⁺ + 1) | (KBr) 2850~3125 1710, 1605 | (CDCl₃) δ: 1.93~2.12(3H, m), 2.29~2.33(1H, m), 2.64(3H, d), 2.80~2.91(2H, m), 3.00(3H, d), 3.87(3H, s), 4.89(1H, d), 4.96(1H, d), 6.94~6.98(2H, m), 7.25(1H, d), 7.87(1H, d), 8.11~8.14(2H, m) |

TABLE 1-2

| Ex. No. | Q | m | n | R³ | R⁴ | R⁵ | Melting point °C. | MS (m/z) | IR (cm⁻¹) | NMR |
|---|---|---|---|---|---|---|---|---|---|---|
| 25 | HCl | 0 | 2 | 4-COOCH₃ | H | H | 187~191 | (CI) 373 (M⁺ + 1) | (KBr) 2400~3100 1720 | (CDCl₃) δ: 1.80~2.36(4H, m), 2.65(3H, d,) 2.70~3.03(5H, m), 3.95(3H, s), 4.94(1H, d), 5.05(1H, d), 7.27(1H, d), 7.88~7.90(1H, m), 8.12~8.24(4H, m) |
| 26 | HCl | 0 | 2 | H | H | H | 207 | (CI) 316 (M⁺ + 1) | (KBr) 1715 | (CDCl₃) δ: 1.87~2.20(3H, m), 2.28~2.38(1H, m), 2.64(3H, d), 2.73~3.07(5H, m), 7.24~7.28(1H, m), 7.43~7.53(2H, m), 7.58~7.65(1H, m), 7.90~7.94(1H, m), 8.10~8.16(2H, m) |
| 27 | HCl | 0 | 2 | 4-Cl | H | H | 188~189 | (CI) 350 (M⁺ + 1) | (Kbr) 1720 | (CDCl₃) δ: 1.87~2.36(4H, m), 2.65(3H, m), 2.69~2.94(2H, m), 2.98(3H, d), 4.88(1H, d), 4.99(1H, d), 7.25(1H, d), 7.43~7.50(2H, m), 7.89(1H, dd), 8.11~8.18(2H, m), 12.64~12.87(1H, brs) |
| 28 | HCl | 0 | 2 | 3-OCH₃ | 4-OCH₃ | H | 202~203 | (CI) 376 (M⁺ + 1) | (KBr) 1720 | (CDCl₃) δ: 1.90~2.35(4H, m), 2.66(3H, d), 2.70~2.91(2H, m), 2.98(3H, d), 3.96(6H, d), 4.87(1H, d), 4.95(1H, d), 6.95(1H, m), 7.22~7.28(1H, m), 7.58~7.62(1H, m), 7.83~7.95(2H, m) |

EXAMPLES 29–34

Six kinds of compounds were obtained by following the procedure of Example 22. The chemical formulae, melting points, IR, MS and NMR data of these compounds are shown in Table 2.

TABLE 2-1

Compound: 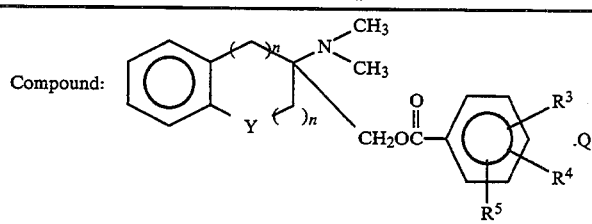

| Ex. No. | Q | Y | m | n | R³ | R⁴ | R⁵ | Melting point °C. | MS (m/z) | IR (cm⁻¹) | NMR |
|---|---|---|---|---|---|---|---|---|---|---|---|
| 29 | HCl | 0 | 0 | 2 | 3-OCH₃ | 4-OCH₃ | 5-OCH₃ | 217~219 | 401 (M⁺) | (KBr) 1710, 1120 | (CDCl₃) δ: 2.35~2.65(5H, m), 2.92~2.98(3H, m), 3.74(3H, s), 3.85(6H, s), 4.00~4.50(2H, m), 4.94(2H, dd), 6.96(1H, d), 7.00~7.10(1H, m), 7.26(2H, s), 7.30~7.40(1H, m), 8.00~8.10(1H, m) |
| 30 | HCl | S | 0 | 2 | 3-OCH₃ | 4-OCH₃ | 5-OCH₃ | 185~186 | 417 (M⁺) | (KBr) 2850~3010 1710, 1585 | (CDCl₃) δ: 2.43~2.53(1H, m) 2.66(3H, d), 2.73~2.79(1H, m), 2.83~2.97(1H, m), 3.04(3H, d), 3.23~3.32(1H, m), 3.91(3H, s), 3.92(6H, s), 5.08(2H, dd), 7.24~7.35(5H, m), 7.43(1H, d) |

TABLE 2-2

| Ex. No. | Q | Y | m | n | $R^3$ | $R^4$ | $R^5$ | Melting point °C. | MS (m/z) | IR (cm$^{-1}$) | NMR |
|---|---|---|---|---|---|---|---|---|---|---|---|
| 31 | — | $CH_2$ | 1 | 0 | 3-$OCH_3$ | 4-$OCH_3$ | 5-$OCH_3$ | 105~106 | (Cl) 386 ($M^+$ + 1) | (KBr) 1700 | ($CDCl_3$) δ: 2.51(6H, s), 3.10(2H, d), 3.20(2H, d), 3.83(3H, s), 3.89(3H, s), 4.41(2H, s), 7.07~7.21(4H, m) |
| 32 | — | $CH_2$ | 1 | 0 | 4-$OCH_3$ | H | H | 85~86 | (Cl) 326 ($M^+$ + 1) | (KBr) 1700 | ($CDCl_3$) δ: 2.49(6H, s), 3.09(2H, d), 3.18(2H, d), 3.85(3H, s), 4.38(2H, s), 6.82~6.90(2H, m), 7.08~7.20(2H, m), 7.25~7.83(2H, m) |
| 33 | — | $CH_2$ | 1 | 0 | 4-Cl | H | H | 119~120 | (Cl) 330 ($M^+$ + 1) | (KBr) 2760~3100 1705,1100 | ($CDCl_3$) δ: 2.48(6H, s), 3.08(2H, d), 3.20(2H, d), 4.41(2H, s), 7.07~7.19(4H, m), 7.32~7.36(2H, m), 7.69~7.73(2H, m) |
| 34 | — | $CH_2$ | 1 | 0 | 4-CO $OCH_3$ | H | H | 104~105 | (Cl) 354 ($M^+$ + 1) | (KBr) 1725,1710 | ($CDCl_3$) δ: 2.49(6H, s), 3.09(2H, d), 3.22(2H, d), 3.94(3H, s), 4.45(2H, s), 7.15(4H, s), 7.82~7.85(2H, m), 8.02~8.05(2H, m) |

EXAMPLE 35

Preparation of 4-dimethylamino-4-[(3,4,5-trimethoxybenzyloxy)methyl]-4,5,6,7-tetrahydro-1-benzothiophene 15 ml of tetrahydrofuran containing 2.57 g of 4-dimethylamino-4-hydroxymethyl-4,5,6,7-tetrahydro-1-benzothiophen obtained in Example 1 was added to an ice-cooled suspension of 60% sodium hydride (0.54 g) in tetrahydrofuran. 15 ml of tetrahydrofuran containing 2.90 g of 3,4,5-trimethoxybenzyl chloride was further added to the reaction mixture, followed by refluxing under heat for 24 hours. After cooling, the reaction mixture was poured into hydrochloric acid solution, and washed with ether. The aqueous phase was added with a sodium hydroxyde solution for making the system basic, followed by extracting with chloroform. After the chloroform phase was washed with water and dried, the solvent was removed. The residue was purified by silica gel column chromatography to obtain 2.79 g of the title compound as a pale yellow oily product.

The melting point, IR, MS and NMR data are shown below.

IR(neat)cm$^{-1}$: 2950, 1595
MS(m/z): 391($M^+$)
NMR ($CDCl_3$) δ: 1.70~2.00(4H, m), 2.24(6H, s), 2.68~2.76(2H, m), 3.54 (1H, d), 3.59 (1H, d), 3.80 (6H, s), 3.82 (3H, s), 4.41 (1H, d), 4.49 (1H, d), 6.46 (2H, s), 7.01 (1H, d), 7.15 (1H, d)

Hydrochloride of the present product: colorless crystals

Melting point: 172°-173° C. (ethanol - ethyl acetate)
The chemical formula is shown below.

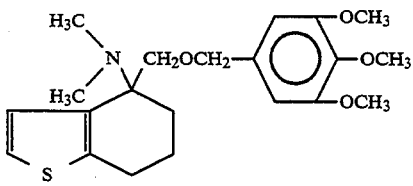

EXAMPLES 36-47

Eleven kinds of compounds were obtained by following the procedure of Example 35. The chemical formulae, melting points, IR, MS and NMR data of these compounds are shown in Tables 3 and 4.

TABLE 3

Compound:

| Ex. No. | $R^3$ | $R^4$ | $R^5$ | Q | Melting point °C. | MS (m/z) | IR (cm$^{-1}$) | NMR |
|---|---|---|---|---|---|---|---|---|
| 36 | 4-Cl | H | H | HCl | 171~172 | (Cl) 336 ($M^+$ + 1) | (KBr) 2100~3100 1110 | ($CDCl_3$) δ: 1.64~1.85(2H, m), 2.03~2.19(1H, m), 2.43~2.60(4H, m), 2.68~3.05(5H, m), 3.65(1H, d), 4.41(1H, d), 4.56(1H, d), 4.72(1H, d), 7.15~7.35 (5H, m), 7.84~7.92(1H, m), 12.29~12.56(1H, brs) |
| 37 | 4-$OCH_3$ | H | H | HCl | 163~164 | (Cl) 332 ($M^+$ + 1) | (KBr) 2850~3100 1610 | ($CDCl_3$) δ: 164~1.75(2H, m), 2.04~2.10(1H, m), 2.47(3H, d), 2.52~2.56(1H, m), 2.75~2.90(2H, m), 3.01 (3H, d), 3.61(1H, d), 3.80(3H, s), 4.36(1H, d), 4.49(1H, d), 4.69(1H, d), 6.85~6.88(2H, m), 7.18~7.26(3H, m), 7.89(1H, d) |

TABLE 3-continued

Compound:

| Ex. No. | R³ | R⁴ | R⁵ | Q | Melting point °C. | MS (m/z) | IR (cm⁻¹) | NMR |
|---|---|---|---|---|---|---|---|---|
| 38 | 3-OCH₃ | 4-OCH₃ | H | — | Oily Product | (CI) 362 (M⁺ + 1) | (Neat) 2750~3100 1595 | (CDCl₃) δ: 1.65~2.01(4H, m), 2.23(6H, s), 2.65~2.75(2H, m), 3.45~3.60(2H, m), 3.82(3H, s), 3.86(3H, s), 4.39(1H, d), 4.46(1H, d), 6.72~6.85(3H, m), 7.00(1H, d), 7.12(1H, d) |
| 39 | 4-CH₃ | H | H | — | Oily Product | (CI) 316 (M⁺ + 1) | (Neat) 2770~2930 1080 | (CDCl₃) δ: 1.73~1.93(4H, m), 2.23(6H, s), 2.32(3H, s), 2.70~2.72(2H, m), 3.54(2H, s), 4.38(1H, d), 4.49(1H, d), 6.99~7.16(6H, m), |
| 40 | H | H | H | HCl | 170~172 | (CI) 302 (M⁺ + 1) | (KBr) 2800~3125 2450~2625 | (CDCl₃) δ: 1.71~1.77(2H, m), 2.04~2.13(1H, m), 2.48(3H, d), 2.55~2.61(1H, m), 2.69~2.88(2H, m), 3.03(3H, d), 3.65(1H, d), 4.43(1H, d), 4.55(1H, d), 4.76(1H, d), 7.19(1H, d), 7.29~7.37(5H, m), 7.90(1H, d) |

TABLE 4-1

Compound:

| Ex. No. | Q | Y | m | n | R³ | R⁴ | R⁵ | Melting point °C. | MS (m/z) | IR (cm⁻¹) | ¹H-NMR |
|---|---|---|---|---|---|---|---|---|---|---|---|
| 41 | HCl | S | 0 | 2 | 3-OCH₃ | 4-OCH₃ | 5-OCH₃ | 91~92 | (EI) 403 (M⁺) | (KBr) 2850~3000 1595, 1510 | (DMSO-d₆) δ: 2.35~2.51(4H, m), 2.68~2.73(1H, m), 2.92(3H, d), 3.04~3.21(2H, m), 3.63(3H, s), 3.75(6H, s), 3.92(1H, d), 4.17 (1H, d), 4.48(2H, dd), 6.60(2H, s), 7.16~7.30(3H, m), 8.12(1H, d) |
| 42 | — | CH₂ | 1 | 1 | 3-OCH₃ | 4-OCH₃ | 5-OCH₃ | Oily Product | (EI) 385 (M⁺) | (Neat) 2930, 1590 1125 | (CDCl₃) δ: 1.80~2.02(2H, m), 2.41(6H, s), 2.57~3.00(4H, m), 3.40(1H, d), 3.45(1H, d), 3.83(9H, s), 4.43(2H, s), 6.55(2H, s), 7.00~7.10(4H, m) |
| 43 | ½ (*) | CH₂ | 1 | 0 | 3-OCH₃ | 4-OCH₃ | 5-OCH₃ | 133~138 | (CI) 372 (M⁺ + 1) | (KBr) 1445, 1125 755 | (CDCl₃) δ: 2.37(6H, s), 2.93(2H, d), 3.09(2H, d), 3.46(2H, s), 3.82(6H, s), 3.83(3H, s), 4.43(2H, s), 6.53(2H, s), 7.10~714(4H, m) |
| 44 | — | CH₂ | 1 | 0 | 4-CH₃ | H | H | Oily Product | (CI) 296 (M⁺ + 1) | (Neat) 2800~3050 1520 | (CDCl₃) δ: 2.33(3H, s), 2.34(6H, S), 2.92(2H, d), 3.06(2H, d), 3.43(2H, s) 4.44(2H, s), 7.10~7.25(8H, m) |

(*): Pamoic Acid

TABLE 4-2

| Ex. No. | Q | Y | m | n | R³ | R⁴ | R⁵ | Melting point °C. | MS (m/z) | IR (cm⁻¹) | ¹H-NMR |
|---|---|---|---|---|---|---|---|---|---|---|---|
| 45 | HCl | CH₂ | 0 | 2 | 3-OCH₃ | 4-OCH₃ | 5-OCH₃ | 184~187 | (EI) 385 (M⁺) | (KBr) 2300~3050 1590,1115 | (CDCl₃) δ: 1.72~2.05(3H, m), 2.45(3H, d), 2.70~2.78(3H, m) 3.11(3H, d), 3.64~3.85(10H, m), 4.38(1H, d), 4.53(1H, d), 5.56(2H, s), 7.12~7.40(3H, m), 8.35(1H, d), 12.29(1H, brs) |
| 46 | HCl | CH₂ | 0 | 1 | 3-OCH₃ | 4-OCH₃ | 5-OCH₃ | 73~74 | (CI) 371 (M⁺) | (KBr) 3360 2850~3030 1590 | (CDCl₃) δ: 2.35~2.53(2H, m), 2.58(3H, d), 2.90(3H, d), 2.95~3.16(2H, m), 3.72(1H, d), 3.83(3H, s), 3.84(6H, s), 4.30(1H, d), 4.44(1H, d), 4.62(1H, d), 6.55(2H, s), 7.26~7.40(3H, m), 7.99~8.02(1H, m) |
| 47 | — | CH₂ | 1 | 0 | 4-OCH₃ | H | H | Oily Product | (CI) 312 (M⁺ + 1) | (Neat) 2780~3070 | (CDCl₃) δ: 2.34(6H, s), 2.91(2H, d), 3.07(2H, d), 3.42(2H, s), |

TABLE 4-2-continued

| Ex. No. | Q | Y | m | n | R³ | R⁴ | R⁵ | Melting point °C. | MS (m/z) | IR (cm⁻¹) | ¹H-NMR |
|---|---|---|---|---|---|---|---|---|---|---|---|
| | | | | | | | | | (M⁺ + 1) | 1090 | 3.78(3H, s), 4.41(2H, s), 6.82~6.85(2H, m), 7.11~7.24(6H, m) |

EXAMPLES 48–65

Compounds of the following nomenclature, chemical formulae, melting points, IR, MS land NMR data were obtained by following the procedure of Example 22.

EXAMPLE 48

4-Dimethylamino-4-[(3,4,5-trimethoxybenzoyloxy)methyl]-cyclopenta[b]thiophene.HCl

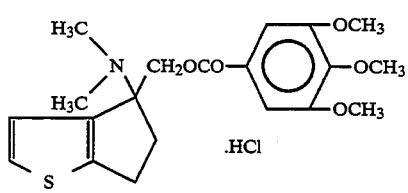

Melting point: 127°–129° C.
IR(KBr)cm⁻¹: 1715, 1335, 1130
MS (m/z): (CI) 392 (M⁺ + 1)
NMR (CDCl₃) δ: 2.70~2.92 (7H, m), 3.05~3.20 (3H, m), 3.91 (3H, s), 3.97 (6H, s), 4.77 (1H, d), 4.37 (1H, d), 7.26 (1H, d), 7.37 (1H, d), 7.45 (2H, s)

EXAMPLE 49

4-Dimethylamino-4-[(3,4,5-trimethoxybenzoyloxy)methyl]-cyclohepta[b]thiophene.HCl

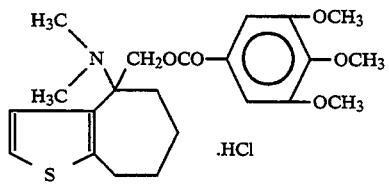

Melting point: 158°–159° C.
IR(KBr)cm⁻¹: 1710
MS (m/z):(CI)420(M⁺ + 1)
NMR (DMSO-d₆) δ: 1.57~2.03(4H, m), 2.25~2.50 (2H, m), 2.67 (3H, d), 2.79 (3H, d), 2.84~2.96 (1H, m), 3.12~3.26 (1H, m), 3.74 (3H, s), 3.87 (6H, s), 4.80 (1H, d), 4.87 (1H, d), 7.33(2H, s), 7.41 (1H, d), 7.67 (1H, d), 10.60~11.00(1H, brs)

EXAMPLE 50

4-(N-ethyl-N-methyl)amino-4-[(3,4,5-trimethoxybenzoyloxy)methyl]-4,5,6,7-tetrahydro-1-benzothiophene

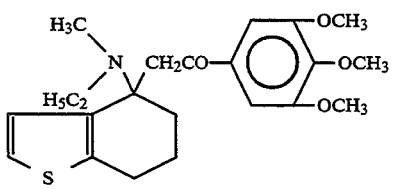

Melting point: 75°–76° C.
IR(KBr)cm⁻¹: 3000~2750, 1720, 1590
MS (m/z):(CI)420(M⁺ + 1)
NMR (CDCl₃) δ: 0.99(3H, t), 2.32~2.44(2H, m), 2.73~2.79(2H, m), 3.88 (3H, s), 3.89 (6H, s), 4.42 (1H, d), 4.55 (1H, d), 7.01 (1H, d), 7.13 (1H, d), 7.19 (2H, s)

EXAMPLE 51

4-Dimethylamino-4-[(3,4,5-trimethoxyphenylacetoxy)methyl]-4,5,6,7-tetrahydro-1-benzothiophene.HCl

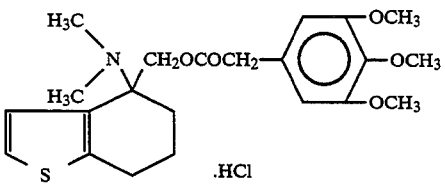

Amorphous
IR(KBr)cm⁻¹: 1745, 1590
MS (m/z):(CI)420(M+1)
NMR (CDCl₃) δ: 1.72–2.10 (4H, m), 2.53 (3H, brs), 2.65~2.93 (5H, m), 3.72~3.90 (11H, m), 4.56~4.73 (2H, m), 6.61 (2H, s), 7.20 (1H, d), 7.80 (1H, d), 12.41 (1H, brs)

EXAMPLE 52

4-Dimethylamino-4-[[3-(3,4,5-trimethoxyphenyl)-propanoyloxy]methyl]-4,5,6,7-tetrahydro-1-benzothiophene.fumaric acid salt

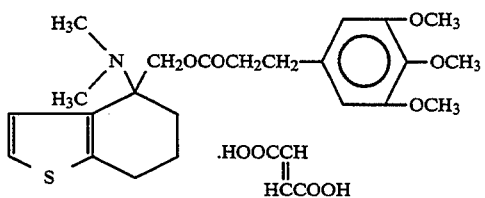

Melting point: 157°–158° C.
IR (KBr)cm⁻¹: 2940~2835, 1745, 1590
MS (m/z): (EI) 433 (M⁺)
NMR (DMSO-d₆) δ: 1.55~1.92(4H, m), 2.14 (6H, s), 2.58~2.78(6H, m), 3.61 (3H, s), 3.73 (6H, s), 4.10 (1H, d), 4.31 (1H, d), 6.49 (2H, s), 6.61 (2H, s), 7.02 (1H, d), 7.21 (1H, d)

EXAMPLE 53

4-Dimethylamino-4-[(3,4,5-trimethoxybenzoyloxy)methyl]-4,5,6,7-tetrahydro-1-benzofuran.maleic acid salt

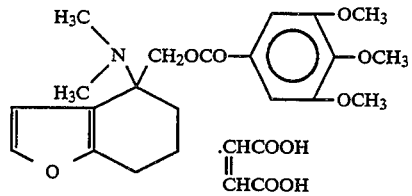

Melting point: 121°–122° C.
IR (KBr)cm$^{-1}$: 1730
MS (m/z):(CI)390(M$^+$+1)
NMR (DMSO-d$_6$) δ: 1.82~2.26(4H, m), 2.52~2.90 (8H, m), 3.15~3.50 (2H, brs), 3.76 (3H, s), 3.85 (6H, s), 4.50 (1H, d), 4.87 (1H, d), 6.04 (2H, s), 6.72(1H, d), 7.25 (2H, s), 7.67(1H, d)

EXAMPLE 54

5-Dimethylamino-5-[(3,4,5-trimethoxybenzoyloxy)methyl]-5,6,7,8-tetrahydro-quinoline.HCl

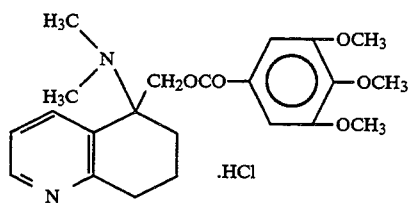

Melting point: 197°–205° C.
IR (KBr)cm$^{-1}$: 1720
MS (m/z): (CI) 401 (M$^+$+1)
NMR (DMSO-d$_6$) δ: 1.82~2.14(2H, m), 2.20~2.40(2H, m), 2.54(3H, brs), 2.85~3.15 (5H, m), 3.74 (3H, s), 3.87 (6H, s), 4.80 (1H, d), 4.90 (1H, d), 4.00~6.00 (2H, brs), 7.28 (2H, s), 7.50~7.60 (1H, m), 8.58~8.66 (1H, m), 8.92~9.02 (1H, m), 11.76~12.00(1H, brs)

EXAMPLE 55

1-Dimethylamino-1-[(3,4,5-trimethoxybenzoyloxy)methyl]cycloheptabenzene

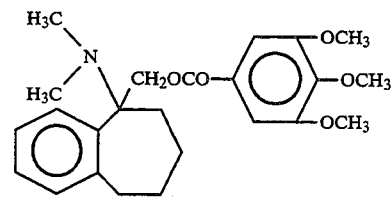

Oily product
IR(neat)cm$^{-1}$: 2940–2785, 1720, 1590
MS (m/z): (CI)414(M$^+$+1)
NMR (CDCl$_3$) δ: 1.35~1.55(1H, m), 1.60~2.08(5H, m), 2.32(6H, s), 2.65 (1H, ddd), 3.40 (1H, ddd), 3.83 (6H, s), 3.89 (3H, s), 4.61 (1H, d), 4.77 (1H, d), 7.08~7.15 (3H, m), 7.25 (2H, s), 7.51~7.55 (1H, m)

EXAMPLE 56

2-Dimethylamino-2-[(3,4,5-trimethoxybenzoyloxy)methyl]-1,2,3,4-tetrahydronaphthalene.HCl

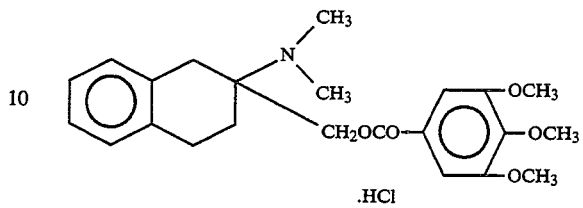

Melting point: 160°–162° C.
IR(KBr) cm$^{-1}$: 1710, 1590
MS (m/z): (EI) 399 (M$^+$)
NMR (CDCl$_3$) δ: 2.42~2.51(2H, m), 2.80~3.07(2H, m), 2.96(6H, s), 3.13 (1H, d), 3.58 (1H, d), 3.92 (3H, s), 3.94 (6H, s), 4.47 (1H, d), 4.55 (1H, d), 7.08~7.23 (4H, m), 7.33 (2H, s), 12.79 (1H, brs)

EXAMPLE 57

6-Chloro-4-dimethylamino-4-[(3,4,5-trimethoxybenzoyloxy)methyl]-2,3-dihydro-4H-1-benzopyran.HCl

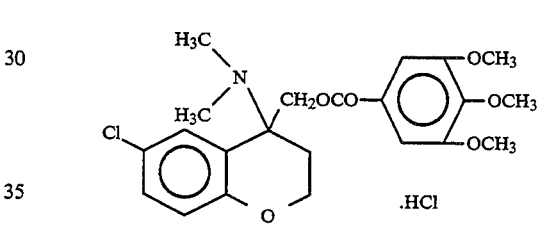

Melting point: 205°–206° C.
IR(KBr) cm$^{-1}$: 1715, 1590, 1335
MS (m/z): (EI) 435 (M$^+$)
NMR (CDCl$_3$) δ: 2.34 (1H, m), 2.48 (1H, m), 2.69 (3H, d), 3.01 (3H, d), 3.91 (3H, s), 3.94 (6H, s), 4.19 (1H, m), 4.40 (1H, m), 5.02 (1H, d), 5.09 (1H, d), 6.91 (1H, d), 7.28 (1H, dd), 7.37 (2H, s), 8.38 (1H, d)

EXAMPLE 58

4-Dimethylamino-6-fluoro-4-[(3,4,5-trimethoxybenzoyloxy)methyl]-2,3-dihydro-4H-1-benzopyran.HCl

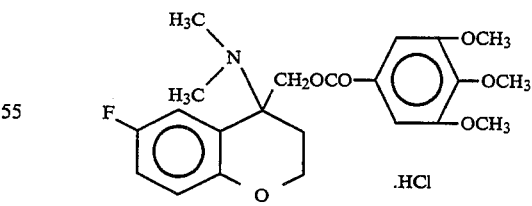

Melting point: 193°–195° C.
IR(KBr) cm$^{-1}$: 3015~2835, 1715, 1595
MS (m/z): (EI) 419 (M$^+$)
NMR (CDCl$_3$) δ: 2.27~2.36(1H, m), 2.39~2.53(1H, m), 2.67(3H, d), 3.02 (3H, d), 3.91 (3H, s), 3.93 (6H, s), 4.18 (1H, ddd), 4.32~4.42 (1H, m), 5.02 (1H, d), 5.12 (1H, d), 6.93 (1H, dd), 7.06 (1H, ddd), 7.35 (2H, s), 8.19 (1H, dd), 13.25 (1H, brs)

EXAMPLE 59

4-Dimethylamino-6-methoxy-4-[(3,4,5-trimethoxybenzoyloxy)methyl]-2,3-dihydro-4H-1-benzopyran.HCl

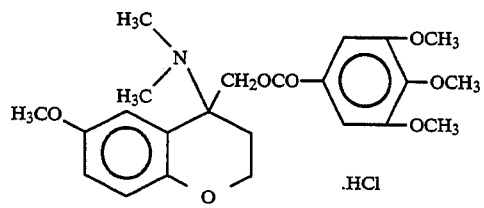

Melting point: 194°–196° C.
IR (KBr) cm$^{-1}$: 1720, 1590, 1505
MS (m/z): (EI) 431 (M+)
NMR (CDCl$_3$) δ: 2.19~2.40 (2H, m), 2.60 (3H, d), 3.06 (3H, d), 3.88 (3H, s), 3.91 (9H, s), 4.11~4.22 (1H, m), 4.25~4.35 (1H, m), 5.19 (2H, s), 6.84~6.94 (2H, m), 7.31 (2H, s), 7.92 (1H, d) 13.17 (1H, brs)

EXAMPLE 60

4-Dimethylamino-6-methyl-4-[(3,4,5-trimethoxybenzoyloxy)methyl]-2,3-dihydro-4H-1-benzopyran.HCl

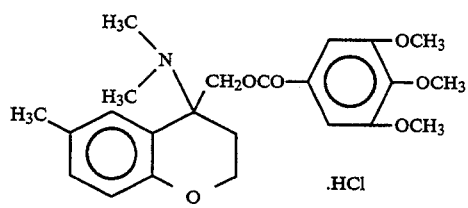

Melting point: 205°–206° C.
IR(KBr) cm$^{-1}$: 1715, 1505, 1330
MS (m/z): (EI) 415 (M+)
NMR (CDCl$_3$) δ: 2.34 (3H, s), 2.37 (2H, m), 2.63 (3H, d), 3.01 (3H, d), 3.91 (3H, s), 3.93 (6H, s), 4.16 (1H, m), 4.33 (1H, m), 5.09 (1H, d), 5.14 (1H, d), 6.85 (1H, d), 7.13 (1H, dd), 7.35 (2H, s), 8.06 (1H, d)

EXAMPLE 61

4-Dimethylamino-2,2-dimethyl-4-[(3,4,5trimethoxybenzoyloxy)methyl]-2,3-dihydro-4H-1-benzopyran

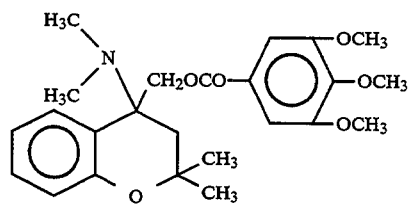

Melting point: 114°–115° C.
IR(KBr)cm$^{-1}$: 1720
MS (m/z) : (EI) 429 (M+)
NMR (CHCl$_3$) δ:1.35(3H, s), 1.37(3H, s), 1.94(1H, d), 2.16(1H, d), 2.24 (6H, s), 3.89 (6H, s), 3.90 (3H, s), 4.46 (1H, d), 4.56 (1H, d), 6.81 (1H, dd), 6.93 (1H, dt), 7.15 (1H, ddd), 7.26 (2H, s), 7.60 (1H, dd)

EXAMPLE 62

6-Chloro-4-dimethylamino-4-[(3,4,5-trimethoxybenzoyloxy)methyl]-2,3-dihydro-4H-1-benzothiopyran.HCl

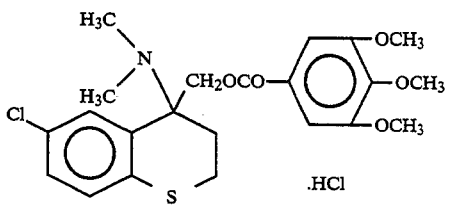

Melting point: 193°–194° C.
IR (KBr) cm$^{-1}$: 1715, 1330, 1215
MS (m/z): (EI) 451 (M+)
NMR (CDCl$_3$) δ: 2.55(1H, m), 2.73(3H, brs),2.81(1H, m), 2.98(1H, m), 3.03 (3H, brs), 3.25 (1H, m), 3.91 (3H, s), 3.94 (6H, s), 4.96 (1H, d), 5.04 (1H, d), 7.19 (1H, d), 7.26 (1H, dd), 7.33 (2H, s), 8.58 (1H, d)

EXAMPLE 63

4-Dimethylamino-6-methoxy-4-[(2,3,4-trimethoxybenzoyloxy)methyl]-2,3-dihydro-4H-1-benzothiopyran.HCl

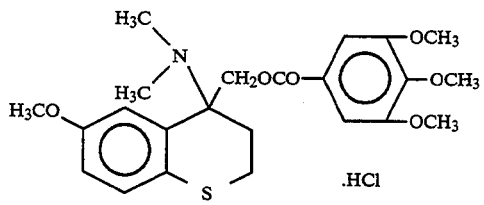

Melting point: 189°–190° C.
IR(KBr) cm$^{-1}$: 1720, 1240, 1130
MS (m/z): (EI) 447 (M+)
NMR (CDCl$_3$) δ:2.44(1H, m), 2.63 (3H, d), 2.71(1H, m), 2.89(1H, m) 3.08 (3H, d), 3.25 (1H, m), 3.90 (8H, s), 3.91 (3H, s), 3.94 (3H, s), 5.07 (1H, d), 5.17 (1H, d), 6.88 (1H, dd), 7.13 (1H, d), 7.26 (2H, s), 8.08 (1H, d)

EXAMPLE 64

4-Dimethylamino-6-methyl-4-[(3,4,5-trimethoxybenzoyloxy)methyl]-2,3-dihydro-4H-1-benzothiopyran.HCl

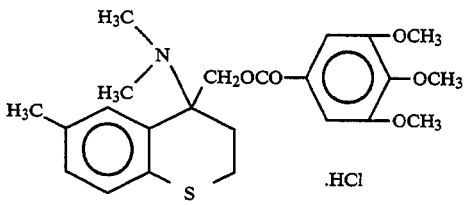

Melting point: 191°–192° C.
IR(KBr) cm$^{-1}$: 1720, 1335, 1130
MS (m/z): (EI) 431 (M+)
NMR (CDCl$_3$) δ:2.38 (3H, s), 2.49 (1H, m), 2.65 (3H, d), 2.71 (1H, m), 2.93 (1H, m), 3.03 (3H, d), 3.24 (1H, m), 3.91 (3H, s), 3.92 (6H, s), 5.02 (1H, d), 5.10 (1H, d), 7.11 (2H, m), 7.29 (2H, m), 8.29 (1H, m)

EXAMPLE 65

4-Dimethylamino-1-methyl-4-[(3,4,5-trimethoxybenzoyloxy)methyl]-1,2,3,4-tetrahydroquinoline

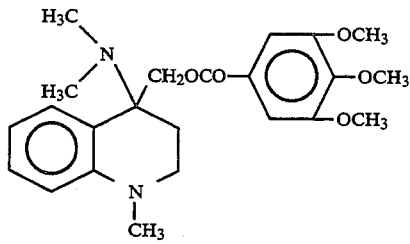

Melting point: 85°–86° C.
IR (KBr) cm⁻¹: 1715, 1330, 1125
MS (m/z): (EI) 414(M+)
NMR (CDCl₃) δ:1.88~2.05 (1H, m), 2.16~2.35 (1H, m), 2.32 (6H, s), 2.88 (3H, s), 3.15~3.32 (2H, m), 3.86 (6H, s), 3.89 (3H, s), 4.42 (1H, d), 4.67 (1H, d), 6.61~6.71 (2H, m), 7.10~7.17 (1H, m), 7.19 (2H, s), 7.56(1H, dd)

EXAMPLE 66

Preparation of 4-dimethylamino-4-[(3,4,5-trimethoxybenzoyloxy)methyl]-2,3-dihydro-4H-1-benzothiopyran-1-oxide The title compound was obtained via the following procedure.

1.13 g of 4-dimethylamino-4-[(3,4,5-trimethoxybenzoyloxy)methyl]-2,3-dihydro-4H-1-benzothiopyran.HCl obtained in Example 30 was dissolved in 110 ml of methylene chloride, to which 525 mg of metachloroperbenzoic acid (70%) was added, followed by stirring for 10 minutes. The reaction mixture was added with saturated aqueous sodium bicarbonate solution, and was subjected to separation. The methylene chloride phase was condenced, and purified through a silica gel column to obtain 739 mg of the title compound as colorless crystals.

The melting point, IR, MS and NMR data are shown below.

Melting point: 146°–148° C.
IR (KBr) cm⁻¹: 1710, 1330, 1220, 1125, 1045
MS (m/z): (EI) 433 (M+)
NMR (CDCl₃) δ: 2.03(1H, ddd), 2.34(6H, s), 2.85~3.15(2H, m), 3.32 (1H, ddd), 3.84 (6H, s), 3.88 (3H, s), 4.40 (1H, d), 4.46 (1H, d), 7.02 (2H, s), 7.46 (1H, ddd), 7.55 (1H, ddd), 7.80 (1H, dd), 8.00 (1H, dd)

The chemical formula is shown below.

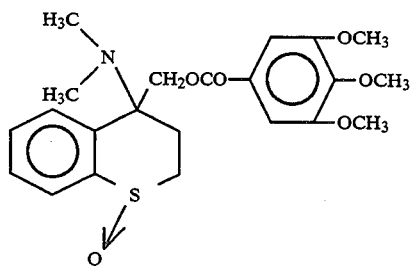

EXAMPLE 67

Preparation of 4-dimethylamino-4-[(3,4,5-trimethoxybenzoyloxy)methyl] -2,3-dihydro-4H-1-benzothiopyran-1,1-dioxide The title compound was obtained via the following procedure.

1.13 g of 4-dimethylamino-4-[(3,4,5-trimethoxybenzoyloxy)methyl]-2,3-dihydro-4H-1-benzothiopyran.HCl obtained in Example 30 was added with 11 ml of 30% hydrogen peroxide and 11 ml of acetic acid, and stirred for 20 hours at room temperature. The reaction solution was neutralized, extracted with methylene chloride, and purified through a silica gel column to obtain 165 mg of the title compound as colorless crystals.

Melting point: 152° C.
MS (m/z):(EI)449(M+)
IR(KBr)cm⁻¹: 1715, 1305, 1220, 1135, 1130, 1000
NMR (CDCl₃) δ: 2.32 (6H, s), 2.44~2.64 (1H, m), 2.85~3.03 (1H, m), 3.29~3.48 (1H, m), 3.53~3.74 (1H, m), 3.83 (6H, s), 3.86 (3H, s), 4.55 (2H, s), 7.00 (2H, s), 7.48 (1H, ddd), 7.58 (1H, ddd), 7.88 (1H, dd), 7.97 (1H, dd)

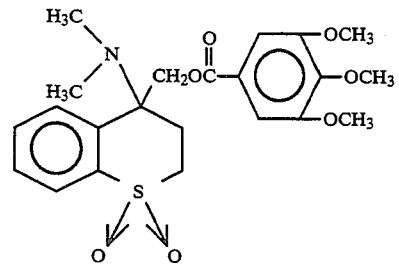

EXAMPLES 68–86

The compounds of the following nomenclature, chemical formulas, melting points, IR, MS and NMR were obtained according to the procedure of Example 35.

EXAMPLE 68

4-Dimethylamino-4-[(3,4,5-trimethoxybenzyloxy)methyl]cyclopenta[b]thiophene

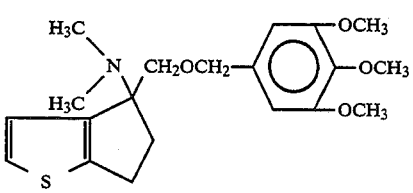

Oily pruduct
IR(neat)cm⁻¹ 1460, 1235, 1125
MS (m/z):(CI)378(M++1)
NMR (CDCl₃) δ: 2.07~2.30(1H, m), 2.21 (6H, s), 2.49~2.71 (1H, m), 2.80~2.94(2H, m), 3.51 (1H, d), 3.59(1H, d), 3.80(6H, s), 3.82 (3H, s), 4.48 (2H, s), 6.49 (2H, s), 6.98 (1H, d), 7.16(1H, d)

EXAMPLE 69

4-Dimethylamino-4-[(3,4,5-trimethoxybenzyloxy)methyl]cyclohepta[b]thiophene.HCl

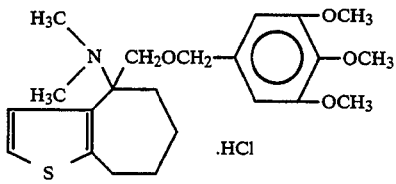

Melting point: 107°–109° C.
IR (KBr) cm$^{-1}$: 1150
MS (m/z): (CI) 406 (M$^+$+1)
NMR (DMSO-d$_6$) δ: 1.45~1.97 (4H, m), 2.17~2.35 (2H, m), 2.55 (3H, d), 2.75 (3H, d), 2.75~2.90 (1H, m), 3.09~3.23 (1H, m), 3.64 (3H, s), 3.77 (6H, s), 3.79 (1H, d), 4.13 (1H, d), 4.47 (1H, d), 4.53 (1H, d), 6.64 (2H, s), 7.37 (1H, d), 7.49(1H, d), 10.00~10.20 (1H, brs)

EXAMPLE 70

4-(N-ethyl-N-methyl)amino-4-[(3,4,5-trimethoxybenzyloxy)methyl]-4,5,6,7-tetrahydro-1-benzothiophene.-fumaric acid salt

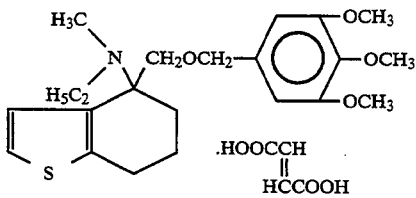

Melting point: 135°–137° C.
IR (KBr) cm$^{-1}$: 3000~2475, 1700, 1595
MS (m/z): (EI) 405 (M$^+$)
NMR (DMSO-d$_6$) δ: 0.99 (3H, t), 1.70~1.98 (4H, m), 2.33 (3H, s) 2.38~2.61 (2H, m), 2.66~2.75 (2H, m), 3.59~3.76 (11H, m), 4.33~4.44 (2H, m), 6.55 (2H, s), 6.59 (2H, s), 7.13 (1H, d), 7.25 (1H, d)

EXAMPLE 71

4-Dimethylamino-4-[(3,4,5-trimethoxybenzyloxy)methyl]-4,5,6,7-tetrahydro-1-benzofuran

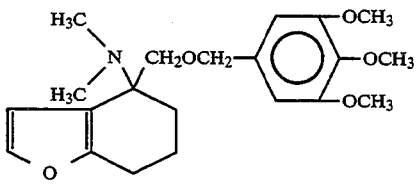

Oily product
IR(neat)cm$^{-1}$: 1130
MS (m/z):(CI)376(M$^+$+1)
NMR (CDCl$_3$) δ: 1.58~2.00(4H, m), 2.30(6H, s), 2.51(2H, m), 3.48 (1H, d), 3.57 (1H, d), 3.80 (6H, s), 3.83 (3H, s), 4.47 (2H, s), 6.50 (2H, s), 6.51 (1H, d), 7.23 (1H, d)

EXAMPLE 72

5-Dimethylamino-5-[(3,4,5-trimethoxybenzyloxy)methyl]-5,6,7,8-tetrahydroquinoline

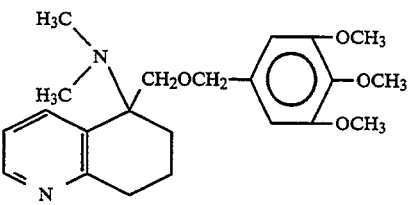

Oily product
IR(neat)cm$^{-1}$: 1130
MS (m/z):(EI)386(M$^+$)
NMR (CDCl$_3$) δ: 1.80~2.00(4H, m), 2.22 (6H, s), 2.83~2.93 (2H, m) 3.50 (1H, d), 3.58 (1H, d), 3.78 (6H, s), 3.82 (3H, s), 4.33 (1H, d), 4.41 (1H, d), 6.39 (2H, s), 7.11 (1H, dd), 8.03 (1H, dd), 8.38 (1H, dd)

EXAMPLE 73

1-Dimethylamino-1-[(3,4,5-trimethoxybenzyloxy)methyl]cycloheptabenzene.HCl

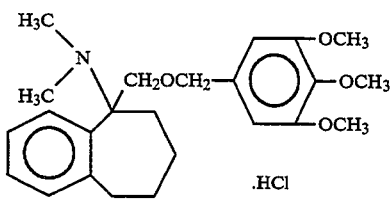

Melting point: 103°–107° C.
IR (KBr) cm$^{-1}$: 3320, 2940, 1595
MS (m/z): (EI)399(M$^+$)
NMR (CDCl$_3$) δ:1.45~1.80(2H, m), 1.84~2.03 (2H, m), 2.12~2.24(1H, m) 2.54 (3H, d), 2.47~2.63 (1H, m), 2.64~2.75(1H, m), 3.03 (3H, d), 3.11~3.25 (1H, m), 3.74 (1H, d), 3.83 (3H, s), 3.85 (6H, s), 4.43 (1H, d), 4.62~4.73 (2H, m), 6.56 (2H, s), 7.14(1H, d), 7.25~7.32 (1H, m), 7.37~7.45(1H, m), 8.23(1H, d)

EXAMPLE 74

2-Dimethylamino-2-[(3,4,5-trimethoxybenzyloxy)methyl]-1,2,3,4-tetrahydronaphthalene.fumaric acid salt

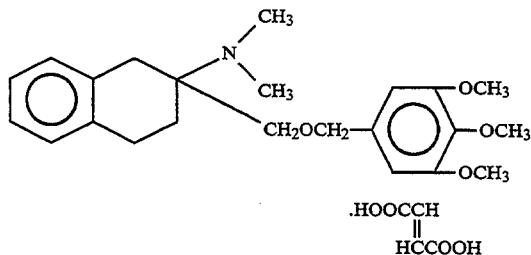

Melting point: 144°–146° C.
IR(KBr)cm$^{-1}$: 2950~2840, 1715, 1680
MS (m/z): (EI) 385 (M$^+$)
NMR (DMSO-d$_6$) δ: 1.83~2.03 (2H, m), 2.50 (6H, s), 2.59~2.88 (2H, m), 2.82 (1H, d), 3.00 (1H, d), 3.44~3.53 (2H, m), 3.64 (3H, s), 3.75 (6H, s), 4.41 (2H, s), 6.55 (2H, s), 6.62 (2H, s), 7.07 (4H, s)

EXAMPLE 75

4-Dimethylamino-4-[(3,4,5-trimethoxybenzyloxy)methyl]-2,3-dihydro-4H-1-benzopyran . 2-(4-hydroxybenzoyl)benzoic acid salt

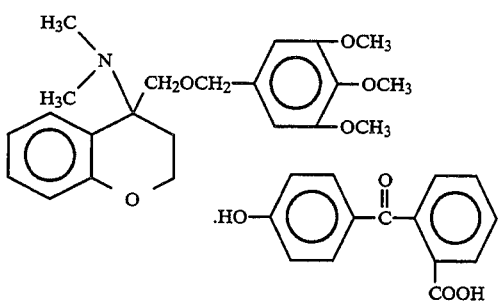

Melting point: 140°-141° C.
IR(KBr) cm$^{-1}$: 1660, 1130
MS (m/z) : (CI) 388 (M$^+$+1)
NMR (DMSO-d$_6$) δ: 1.90~2.00(1H, m), 2.06~2.16 (1H, m), 2.16(6H, s), 3.10~3.60 (1H, brs), 3.62 (3H, s), 3.68 (1H, d), 3.70 (6H, s), 3.72 (1H, d), 4.08~4.26 (2H, m), 4.33 (1H, d), 4.40 (1H, d), 6.50 (2H, s), 6.74 (1H, dd), 6.78~6.90 (3H, m), 7.07~7.15 (1H, m), 7.34 (1H, dd), 7.44~7.54 (3H, m), 7.57~7.73(2H, m), 7.95(1H, dd), 10.30~10.70(1H, brs)

EXAMPLE 76

6-Chloro-4-dimethylamino-4-[(3,4,5-trimethoxybenzyloxy)methyl]-2,3-dihydro-4H-1-benzopyran.HCl

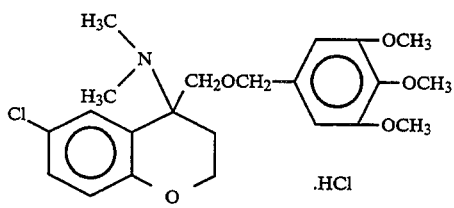

Melting point: 176°-177° C.
IR (KBr) cm$^{-1}$: 1595, 1510, 1130
MS (m/z): (EI) 421 (M+)
NMR (CDCl$_3$) δ: 2.25(1H, m), 2.53(3H, d), 2.61(1H, m), 3.06(3H, d), 3.83 (3H, s), 3.85 (6H, s), 3.87 (1H, d), 3.97 (1H, m), 4.35 (1H, m), 4.41 (1H, d), 4.59 (1H, d), 4.70 (1H, d), 6.53 (2H, s), 6.84 (1H, d), 7.23 (1H, dd), 8.35 (1H, d)

EXAMPLE 77

4-Dimethylamino-6-fluoro-4-[(3,4,5-trimethoxybenzyloxy)methyl]-2,3-dihydro-4H-1-benzopyran . 2-(4-hydroxybenzoyl)benzoic acid salt

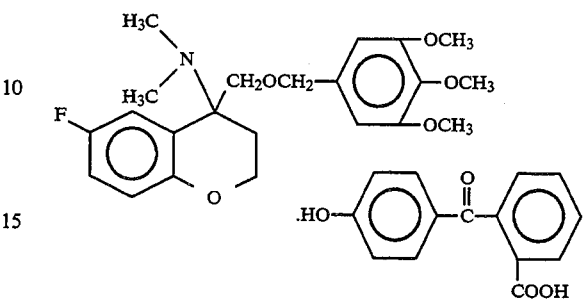

Melting point: 162°-163° C.
IR(KBr) cm$^{-1}$: 3455, 1660, 1590
MS (m/z):(EI)405(M+)
NMR (DMSO-d$_6$) δ: 1.84~1.95(1H, m), 2.09~2.22 (1H, m), 2.18(6H, s), 3.63 (3H, s), 3.64~3.72 (2H, m), 3.71 (6H, s), 4.08~4.22 (2H, m), 4.35 (1H, d), 4.41 (1H, d), 6.50 (2H, s), 6.74~6.84 (3H, m), 6.92~7.02 (1H, m), 7.23~7.35(2H, m), 7.46~7.52 (2H, m), 7.60(1H, ddd), 7.68 (1H, ddd), 7.95 (1H, dd), 10.36 (1H, brs)

EXAMPLE 78

4-Dimethylamino-6-methoxy-4-[(3,4,5-trimethoxybenzyloxy)methyl]-2,3-dihydro-4H-1-benzopyran.HCl

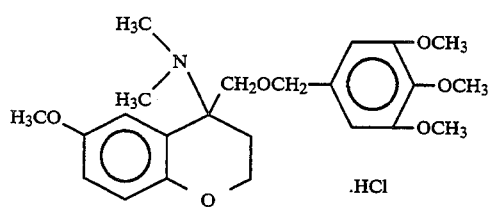

Melting point: 76°-79° C.
IR(KBr)cm$^{-1}$: 1595, 1500
MS (m/z): (EI) 417 (M+)
NMR (CDCl$_3$) δ: 2.17(1H, ddd),2.48 (3H, d), 2.57~2.66(1H, m), 3.08(3H, d), 3.81~3.99 (14H, m), 4.23~4.32 (1H, m), 4.39 (1H, d), 4.64~4.75 (2H, m), 6.53 (2H, s), 6.79 (1H, d), 6.86 (1H, dd), 7.88 (1H, d), 12.66 (1H, brs)

EXAMPLE 79

4-Dimethylamino-6-methyl-4-[(3,4,5-trimethoxybenzyloxy)methyl]-2,3-dihydro-4H-1-benzofuran.HCl

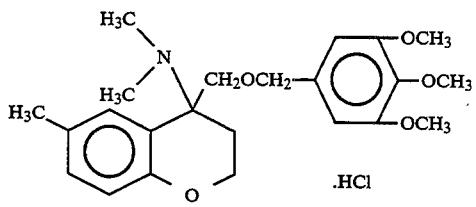

Melting point: 75°-76° C.
IR(KBr)cm$^{-1}$: 1590, 1510, 1225
MS (m/z): (EI) 401 (M+)

NMR (CDCl₃) δ: 2.20 (1H, m), 2.34 (3H, s), 2.47 (3H, d), 2.62 (1H, m), 3.08 (3H, d), 3.83 (3H, s), 3.85 (6H, s), 3.88 (1H, d), 3.96 (1H, m), 4.30 (1H, m), 4.39 (1H, d), 4.64 (1H, d), 4.72 (1H, d), 6.54 (2H, s), 6.77 (1H, d), 7.07 (1H, dd), 8.05(1H, d)

EXAMPLE 80

4-Dimethylamino-2,2-dimethyl-4-[(3,4,5-trimethoxybenzyloxy)methyl]-2,3-dihydro-4H-1-benzopyran

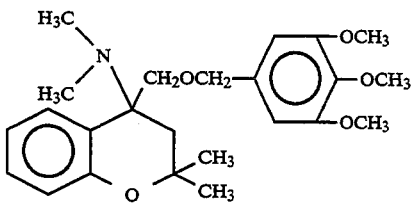

Oily product
IR(neat)cm⁻¹: 1590, 1130, 760
MS (m/z): (EI) 415 (M+)
NMR (CDCl₃) δ: 1.23(3H, s), 1.42(3H, s), 1.96(1H, d), 2.07 (1H, d), 2.18 (6H, s), 3.51 (1H, d), 3.76 (1H, d), 3.81 (6H, s), 3.83 (3H, s), 4.44 (2H, s), 6.51 (2H, s), 6.79 (1H, dd), 6.90 (1H, ddd), 7.13 (1H, ddd), 7.50 (1H, dd)

EXAMPLE 81

6-Chloro-4-dimethylamino-4-[(3,4,5-trimethoxybenzyloxy)methyl]-2,3-dihydro-4H-1-benzothiopyran.HCl

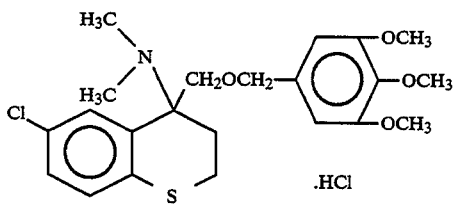

Melting point: 135°–136° C.
IR (KBr) cm⁻¹: 1590, 1465, 1130
MS (m/z): (EI) 437 (M+)
NMR (CDCl₃) δ: 2.16 (1H, m), 2.55 (3H, d), 2.96 (2H, m), 3.02 (1H, m), 3.09 (3H, d), 3.81 (1H, d), 3.83 (3H, s), 3.86 (6H, s), 4.40 (1H, d), 4.54 (1H, d), 4.69 (1H, d), 6.54 (2H, s), 7.11 (1H, d), 7.20 (1H, dd), 8.59 (1H, d)

EXAMPLE 82

4-Dimethylamino-6-methoxy-4-[(3,4,5-trimethoxybenzyloxy)methyl]-2,3-dihydro-4H-1-benzothiopyran.HCl

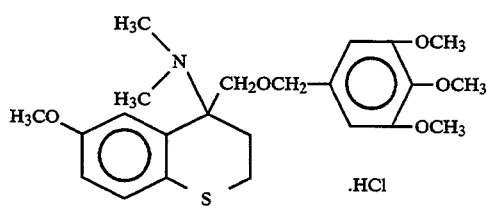

Melting point: 91°–92° C.
(KBr) cm⁻¹: 1120
MS(m/z): (EI)433(M+)
(DMSO-d₆) δ: 2.30~2.50 (4H, m), 2.64~2.76 (1H, m), 2.92 (3H, d), 2.97~3.19 (2H, m), 3.64 (3H, s), 3.75 (6H, s), 3.77 (3H, s), 3.91 (1H, d), 4.19 (1H, d), 4.45 (1H, d), 4.51 (1H, d), 6.61 (2H, s), 6.91 (1H, dd), 7.14 (1H, d), 7.78 (1H, d), 10.95~11.08(1H, brs)

EXAMPLE 83

4-Dimethylamino-6-methyl-4-[(3,4,5-trimethoxybenzyloxy)methyl]-2,3-dihydro-4H-1-benzothiopyran.HCl

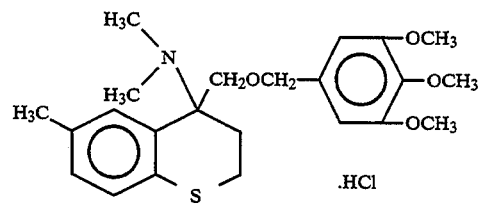

Melting point: 136°–137° C.
IR(KBr)cm⁻¹: 1590, 1120, 1100
MS (m/z): (EI) 417 (M+)
NMR (CDCl₃) δ:2.12~2.30 (1H, m), 2.38 (3H, s), 2.48 (3H, d), 2.79~2.95 (1H, m), 2.94~3.10 (2H, m), 3.10 (3H, d), 3.81(1 H, d), 3.84 (3H, s), 3.86 (6H, s), 4.37 (1H, d), 4.59(1 H, d), 4.71 (1H, d), 6.54 (2H, s), 7.05 (2H, s), 8.32(1H, s)

EXAMPLE 84

4-Dimethylamino-1-methyl-4-[(3,4,5-trimethoxybenzyloxy)methyl]-1,2,3,4-tetrahydroquinoline

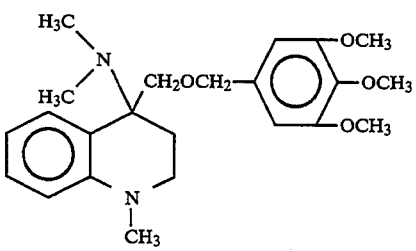

Oily product
IR(neat)cm⁻¹: 1505, 1330, 1130
MS (m/z):(EI)400(M+)
NMR (CDCl₃) δ: 2.00~2.19(2H, m), 2.29(6H, s), 2.85(3H, s), 3.10~3.27 (2H, m), 3.64 (2H, s), 3.80 (6H, s), 3.82 (3H, s), 4.36 (1H, d), 4.43 (1H, d), 6.46 (2H, s), 6.57~6.69 (2H, m), 7.08~7.14 (1H, m), 7.47 (1H, dd)

EXAMPLE 85

4-Dimethylamino-4-[(3,4,5-trimethoxybenzyloxy)methyl]-2,3-dihydro-4H-1-benzothiopyran-1-oxide

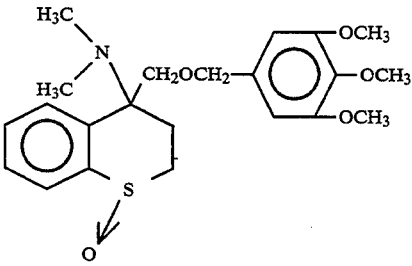

Oily product
IR(neat)cm⁻¹: 1590, 1460, 1130
MS (m/z): (CI) 420 (M+ +1)

NMR (CDCl₃) δ: 2.11 (1H, ddd), 2.26 (6H, s), 2.88 (1H, ddd), 3.05 (1H, ddd), 3.30 (1H, ddd), 3.50 (1H, d), 3.67 (1H, d), 3.77 (6H, s), 3.81 (3H, s), 4.22 (1H, d), 4.35 (1H, d), 6.29 (2H, s), 7.41 (1H, ddd), 7.51 (1H, ddd), 7.74(1H, dd), 7.91 (1H, dd)

EXAMPLE 86

4-Dimethylamino-4-[(3,4,5-trimethoxybenzyloxy)methyl]-2,3-dihydro-4H-1-benzothiopyran-1,1-dioxide

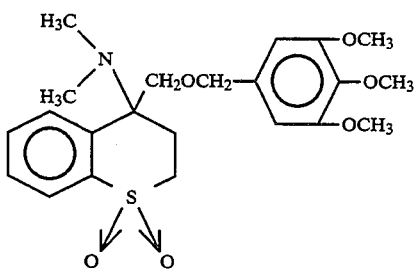

Amorphous
IR(KBr)cm⁻¹: 1590, 1290, 1130
MS (m/z): (EI) 435 (M+)
NMR (CDCl₃) δ: 2.24(6H, s), 2.52(1H, ddd), 2.77 (1H, ddd), 3.33(1H, ddd), 3.61 (1H, d), 3.78 (1H, d), 3.85~3.80 (1H, m), 3.79 (6H, s), 3.82 (3H, s), 4.25 (1H, d), 4.37 (1H, d), 7.26 (2H, s), 7.44 (1H, ddd), 7.52 (1H, ddd), 7.80 (1H, dd), 7.93 (1H, dd)

EXAMPLE 87

Formulation of Preparation Example 1

| Compound of Example 22 | 20 g |
|---|---|
| Lactose | 315 g |
| Corn starch | 125 g |
| Crystalline cellulose | 25 g |

The ingredients indicated above were blended to form a uniform mixture, to which 200 ml of 7.5% aqueous hydroxypropylcellulose solution was added, and then passed an extruder equipped with a screen of 0.5 mm in diameter to prepare granules. Immediately thereafter, the granules were rounded with a marumerizer and dried to obtain a granule preparation.

EXAMPLE 88

Formulation of Preparation Example 2

| Compound of Example 29 | 20 g |
|---|---|
| Lactose | 100 g |
| Corn starch | 36 g |
| Crystalline cellulose | 30 g |
| Carboxymethylcellulose calcium | 10 g |
| Magnesium stearate | 4 g |

The ingredients indicated above were blended to form a uniform mixture, and prepared into tablets each weighing 200 mg with a single-shot tableting machine equipped with a pestle having a diameter of 7.5 mm.

EXAMPLE 89

Formulation of Preparation Example 3

| Compound of Example 41 | 100 mg |
|---|---|
| Sodium acetate | 2 mg |
| Acetic acid (to adjust pH to 5.8) | suitable amount |
| Purified water | suitable amount |
| Total: | 10 ml/vial |

The above formulation was prepared into an injection preparation by a method known per se.

TEXT EXAMPLES

Test 1 Accelerating Action of Gastrointestinal Motility

The test was performed according to the method of Itoh et al. (Am. J. Dig. Dis. 22, 117–124, 1977). In detail, laparotomy was made to male-dogs (body weight: 9–10 kg) under anesthesia with Nembutal (30 mg/kg, i.v.). Force transducers (F-121S, manufactured by Star Medical Co.) were implanted in the direction so that the contraction of circular muscle could be monitored on serosa of gastric body, gastric antrum (about 3 cm proximal to the annular pylorus), duodenum and jejunum. In addition, a silicone tube was inserted from the right external carotid artery, and the tube was indwelled in the superior vena cava. The transducers and the silicone tube were subcutaneously exteriorized out of the body.

The dog was submitted to the test with consciousness and without restraint after about 3 weeks from the operation.

The contractile signals from each transducer were amplified with an amplifier (RTA-1200; manufactured by Nippon Koden Co.), and recorded with a recording apparatus and a computer. The test compounds were dissolved in the saline and intravenously administered (0.5 ml/kg) to the dog through a silicone tube about 10 minutes after the termination of the gastrointestinal inter digestive migrating contractions(IMC) in the antrum.

Evaluation Method

Contracle signals amplified as analog voltage were converted to digital signals, which were integrated to calculate the motor activity. The quantity of work which allows to maintain the 1 V variation in voltage for 6 seconds was counted as 1 unit, and the moter index in the period of 30 minutes after the administration of the test compound was obtained. The thus calculated moter index was compared with the moter index obtained after the saline was administered.

The results are shown in Table 5.

TABLE 5

| Test Compounds | Dose (mg/Kg) | Moter Index Ratio* |
|---|---|---|
| Example 22 | 3 | 2.2 |
| Example 29 | 3 | 1.7 |
| Example 30 | 3 | 1.6 |
| Example 35 | 3 | 1.2 |
| Example 41 | 3 | 2.1 |
| Example 49 | 3 | 1.3 |
| Example 69 | 3 | 1.6 |
| Example 75 | 3 | 1.2 |
| Control compound (trimebutine maleate) | 3 | 1.0 |

*The moter index of the control compound = 1

Test 2 Toxicity Test

Groups of 4–5 week old ICR mice, each group consisting of 6 mice, were provided for the test. The compounds obtained in Examples 22, 29 and 41 were respectively suspended in 5% gum arabic and each was orally administered to the mice at a dose of 500 mg/kg. The mice were observed for 1 week. No death was found in any of the dosage groups.

INDUSTRIAL APPLICABILITY

Since the compounds of present invention have the activity of accelerating the gastrointestinal contraction, in other words, they improve the gastrointestinal motility significantly, while they are very safe, they have the utility in the medical field of treating the gastrointestinal disorders and the like.

We claim:

1. A trialkylamine derivative represented by the formula (1) or a pharmaceutically acceptable salt thereof:

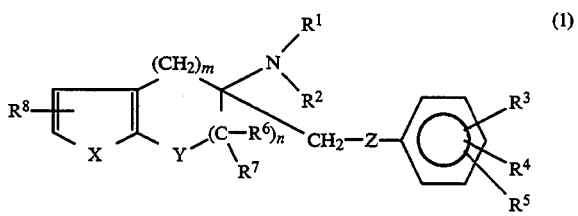

wherein $R^1$ and $R^2$ may be the same or different from each other and each represents lower alkyl;

$R^3$, $R^4$ and $R^5$ may be the same or different from one another and each represents hydrogen, lower alkyl, lower alkoxy, lower alkoxycarbonyl or halogen;

$R^6$ and $R^7$ may be the same or different from each other and each represents hydrogen or lower alkyl;

$R^8$ represents hydrogen, lower alkyl, lower alkoxy or halogen;

X represents oxygen, sulfur or —CH=CH—;

Y represents oxygen, sulfur or methylene;

Z represents —OCO(CH$_2$)$_p$~ or —OCH$_2$(CH$_2$)$_p$~ (wherein p represents a number of 0 to 4 and symbol ~ represents the linkage with a benzene ring);

m is zero and n is 1,2 or 3, provided that the case where m is 0, n is 1 or 2, $R^1$ and $R^2$ represent each methyl, X represents —CH=CH—, Y represents —CH$_2$—, and Z represents —O—CO~ is excluded.

2. An aminoalcohol derivative represented by the formula (2) or a salt thereof:

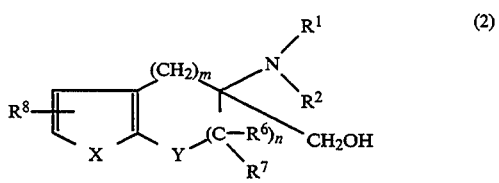

wherein $R^1$ and $R^2$ are the same or different from each other and each represents lower alkyl, $R^6$ and $R^7$ may be the same or different from each other and each represents hydrogen or lower alkyl, $R^8$ represents hydrogen, lower alkyl, lower alkoxy or halogen, X represents oxygen, sulfur or —CH=CH—;

Y represents oxygen, sulfur or methylene;

m is zero and n is 1, 2 or 3, provided that the case where X represents —CH=CH—, Y represents —CH$_2$—, m is 0 and n is 1 or 2 is excluded.

3. A pharmaceutical composition as an ameliorant for gastrointestinal motility containing, as its active ingredient, an effective amount of a trialkylamine derivative represented by the formula (1) or a pharmaceutically acceptable salt thereof:

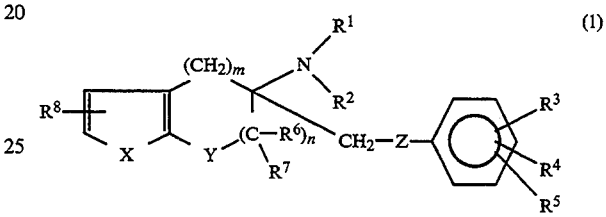

wherein $R^1$ and $R^2$ may be the same or different from each other and each represents lower alkyl;

$R^3$, $R^4$ and $R^5$ may be the same or different from one another and each represents hydrogen, lower alkyl, lower alkoxy, lower alkoxycarbonyl or halogen;

$R^6$ and $R^7$ may be the same or different from each other and each represents hydrogen or lower alkyl;

$R^8$ represents hydrogen, lower alkyl, lower alkoxy or halogen;

X represents oxygen, sulfur or —CH=CH—;

Y represents oxygen, sulfur or methylene;

Z represents —OCO(CH$_2$)$_p$~ or —OCH$_2$(CH$_2$)$_p$~ (wherein p represents a number of 0 to 4 and symbol ~ represents the linkage with a benzene ring);

m is zero and n is 1, 2 or 3, provided that the case where m is 0, n is 1 or 2, $R^1$ and $R^2$ represent each methyl, X represents —CH=CH—, Y represents —CH$_2$—, and Z represents —O—CO~ is excluded; and a pharmaceutically acceptable carrier.

4. A compound as claimed in claim 1 which is 4-dimethylamino-4-[(3,4,5-trimethoxybenzoyloxy)methyl]-4,5,6,7-tetrahydro-1-benzothiophene.

5. The composition of claim 3 wherein the trialkylamine is 4-dimethylamino-4-[(3,4,5-trimethoxybenzoyloxy)methyl]-4,5,6,7-tetrahydro-1-benzothiophene.

* * * * *